United States Patent
Wahlstrand et al.

(10) Patent No.: US 8,688,223 B2
(45) Date of Patent: Apr. 1, 2014

(54) IMPLANTABLE MEDICAL DEVICE IMPEDANCE MEASUREMENT MODULE FOR COMMUNICATION WITH ONE OR MORE LEAD-BORNE DEVICES

(76) Inventors: John D. Wahlstrand, Shoreview, MN (US); James J. St. Martin, Zumbrota, MN (US)

( * ) Notice: Subject to any disclaimer, the term of this patent is extended or adjusted under 35 U.S.C. 154(b) by 320 days.

(21) Appl. No.: 12/912,317

(22) Filed: Oct. 26, 2010

(65) Prior Publication Data
US 2012/0101545 A1    Apr. 26, 2012

(51) Int. Cl.
*A61N 1/08* (2006.01)

(52) U.S. Cl.
USPC ............... 607/60; 607/27; 607/28; 607/29; 607/59; 607/116

(58) Field of Classification Search
USPC ................... 607/27–29, 116, 59–60
See application file for complete search history.

(56) References Cited

U.S. PATENT DOCUMENTS

| | | | |
|---|---|---|---|
| 6,516,227 | B1 | 2/2003 | Meadows et al. |
| 7,391,257 | B1 | 6/2008 | Denison et al. |
| 7,493,174 | B2 | 2/2009 | Belalcazar et al. |
| 7,640,060 | B2 | 12/2009 | Zdeblick |
| 2006/0064149 | A1 | 3/2006 | Belacazar et al. |
| 2008/0039916 | A1 | 2/2008 | Colliou et al. |
| 2008/0114230 | A1 | 5/2008 | Addis |
| 2008/0154328 | A1 | 6/2008 | Thompson et al. |
| 2008/0294218 | A1 | 11/2008 | Savage et al. |
| 2008/0312726 | A1 | 12/2008 | Frank et al. |
| 2009/0018632 | A1 | 1/2009 | Zdeblick et al. |
| 2009/0054946 | A1 | 2/2009 | Sommer et al. |
| 2009/0062880 | A1 | 3/2009 | Li et al. |
| 2009/0192572 | A1* | 7/2009 | Dal Molin et al. .............. 607/59 |
| 2009/0228071 | A1* | 9/2009 | Bourget .......................... 607/60 |
| 2009/0287266 | A1* | 11/2009 | Zdeblick ........................ 607/5 |
| 2010/0016928 | A1 | 1/2010 | Zdeblick et al. |

FOREIGN PATENT DOCUMENTS

| | | |
|---|---|---|
| WO | 2007075974 A2 | 7/2007 |
| WO | 2009131749 A2 | 10/2009 |

OTHER PUBLICATIONS

International Search Report and Written Opinion of PCT/US2011/057361, dated Mar. 6, 2012, 11 pp.
International Preliminary Report on Patentability from international application No. PCT/US2011/057361, dated May 10, 2013, 9 pp.

* cited by examiner

*Primary Examiner* — Joseph Stoklosa

(57) ABSTRACT

Example techniques for communicating between two medical devices are described. One medical device may be an implantable medical device. Another medical device may be a lead-borne implantable medical device. The lead-borne implantable medical device may be referred to as a satellite. The implantable medical device may measure impedance of a path including at least two electrodes, at least one of which is on the lead, using an impedance measurement module. In some example implementations of this disclosure, the implantable medical device may also use the impedance measurement module to communicate with the satellite on the lead.

31 Claims, 9 Drawing Sheets

IMPLANTABLE MEDICAL DEVICE IMPEDANCE MEASUREMENT MODULE FOR COMMUNICATION WITH ONE OR MORE LEAD-BORNE DEVICES

TECHNICAL FIELD

The disclosure relates to communication between an implantable medical device and one or more devices carried by an implantable lead that is connected to the implantable medical device.

BACKGROUND

Implantable medical devices (IMDs) may be configured to provide therapy to and/or sense physiological parameters of an individual in which the IMD is implanted. As one example, an IMD may be configured to provide pacing and/or defibrillation signals to the heart. Additionally or alternatively, an IMD may be configured to sense electrical signals attendant to depolarization and repolarization of the heart.

To provide electrical stimulation therapy and to sense electrical signals, the IMD may be coupled to one or more leads, each of which may include one or more electrodes. Typically, each of the electrodes is coupled to the IMD via a respective conductor within the lead. To sense other physiological parameters, an IMD may be coupled to one or more other sensors, such an accelerometer, a strain gauge, a pressure sensitive-capacitor, an optical perfusion sensor, an oxygen saturation sensor, an ultrasonic flow sensor, a thermistor, or an antimony electrode. In some cases, an IMD is coupled to such a sensor by a lead that also carries one or more electrodes, e.g., via two or more conductors within the lead. Furthermore, in order to reduce the number of conductors traversing the full length of a lead, it has been proposed to include one or more switching devices at relatively distal locations on the lead, the switching device or devices selectively couple two or more conductors of the lead to a greater number of electrodes.

Sensors and switching devices are examples of lead-borne devices, referred to herein as "satellites," that communicate with an IMD to which the satellite is connected by a lead. For example, an IMD may transmit a signal to "wake-up" the satellite. For sensors, the IMD may transmit a command to cause the satellite to perform a measurement, and receive the measurement from the satellite. For switching devices, the IMD may provide a command that selects which electrodes are to be coupled to the IMD for delivery of electrical stimulation or sensing.

SUMMARY

In general, the disclosure describes example techniques for a first implantable medical device (IMD) to communicate with at least a second implantable medical device. In some examples, the second implantable medical device may be carried by an implantable medical lead coupled to the first medical device. In these examples, the second medical device may be considered to as a lead-borne medical device. Also, to further clarify that the second medical device is separate from the first medical device, the second medical device may be referred to as a satellite, and the first medical device may be referred to as a medical device. Examples of the satellite include, but are not limited to, a switching device, an accelerometer, a strain gauge, a pressure sensitive-capacitor, an optical perfusion sensor, an oxygen saturation sensor, an ultrasonic flow sensor, a thermistor, or an antimony electrode. Examples of the medical device include, but are not limited to, cardiac devices such as pacemakers and defibrillators.

In some examples, the medical device may include an impedance measurement module to measure the impedance of an electrical path that includes at least two electrodes, where one of the electrodes is on a lead coupled to the medical device. In some of the example implementations described in this disclosure, the impedance measurement module may be utilized to measure impedance, and may also be utilized to communicate with one or more satellites formed within the one or more leads. For example, the medical device may measure impedance of an electrical path that includes two electrodes utilizing the impedance measurement module, and may also transmit signals to and receive signals from the satellites utilizing the impedance measurement module.

The impedance measurement module may include a current source or a voltage source, referred to as a source, for impedance measurements. The impedance measurement module may also include switches for selection between the different electrodes. To measure impedance of a path that includes at least two electrodes, the impedance measurement module or another processor or circuit may selectively close switches to couple the impedance measurement module to the electrodes. The impedance measurement module may generate, with the source, an impedance measurement signal. The impedance measurement module may measure the impedance of the electrical path that includes the electrodes based on the impedance measurement signal.

To generate the impedance measurement signal, the source, e.g., voltage source or current source, of the impedance measurement module may generate a voltage or current between the electrodes. For example, the source may output a current that flows to a first electrode, out of the first electrode and through tissue, back into a second electrode, and back to the source. To measure the impedance, the impedance measurement module may measure a voltage, if the source generated a current, or measure the current, if the source generated a voltage. The impedance measurement module may then divide the measured voltage with the generated current or the generated voltage with the measured current to determine the impedance.

To communicate with the satellites, as one example, the impedance measurement module of the IMD may generate a communication signal. In some of the example implementations of this disclosure, the impedance measurement module may use the same source used to generate the impedance measurement signal to generate the communication signal. For example, the impedance measurement module may modulate the current generated by a current source, or the voltage generated by a voltage source to transmit signals to the satellites. In this example, the current source or voltage source used to generate the communication signal to communicate with the satellites may be the same current source or voltage source used to generate the impedance measurement signal. Also to communicate with the satellites, the IMD may selectively close switches to transmit signals to and receive signals from the satellites, and may include circuitry to detect modulation of a signal by the satellites for communication to the IMD. In this manner, the IMD may be able to communicate with satellites formed within the lead utilizing circuitry that is already being used for impedance measurements.

In one example, aspects of this disclosure are related to a method comprising generating, with a source of an impedance measurement module within a first implantable medical device, an impedance measurement signal, measuring, with the impedance measurement module, an impedance of an electrical path that includes at least two electrodes based on the impedance measurement signal, wherein at least one of the electrodes is carried by a lead coupled to the first implantable medical device, and generating, with the source of the impedance measurement module, a communication signal for communication between the first implantable medical device and a second implantable medical device that is carried by the lead.

In one example, aspects of this disclosure are related to an implantable medical device comprising an impedance measurement module that comprises a source and is configured to generate an impedance measurement signal with the source, and measure an impedance of an electrical path that includes at least two electrodes based on the impedance measurement signal, wherein at least one of the electrodes is carried by a lead coupled to the implantable medical device, and a processor configured to generate, with the source of the impedance measurement module, a communication signal for communication between the implantable medical device and a lead-borne implantable medical device that is carried by the lead.

In one example, aspects of this disclosure are related to a medical system comprising a lead-borne implantable medical device that is carried by a lead, an implantable medical device coupled to the lead-borne medical device via the lead, the implantable medical device comprising an impedance measurement module that comprises a source and is configured to generate an impedance measurement signal with the source, and measure an impedance of an electrical path that includes at least two electrodes based on the impedance measurement signal, wherein at least one of the electrodes is carried by a lead coupled to the implantable medical device, and a processor configured to generate, with the source of the impedance measurement module, a communication signal for communication between the implantable medical device and the lead-borne implantable medical device that is carried by the lead.

In one example, aspects of this disclosure are related to a computer-readable storage medium comprising instructions that cause one or more processors, within an implantable medical device, to generate, with a source of an impedance measurement module within the implantable medical device, an impedance measurement signal, measure, with the impedance measurement module, an impedance of an electrical path that includes two electrodes based on the impedance measurement signal, wherein at least one of the electrodes is carried by a lead coupled to the implantable medical device, and generate, with the source of the impedance measurement module, a communication signal for communication between the implantable medical device and a lead-borne implantable medical device that is carried by the lead.

In one example, aspects of this disclosure are related to a medical system comprising a first implantable medical device, and a second implantable medical device that is within or carried by a lead coupled to the first implantable medical device, wherein the first implantable medical device comprises means for measuring impedance, wherein the means for measuring impedance comprises a means for generating an impedance measurement signal, means for measuring an impedance of an electrical path that includes at least two electrodes based on the impedance measurement signal, wherein at least one of the electrodes is carried by a lead coupled to the first implantable medical device, and wherein the means for measuring impedance further comprises means for generating a communication signal for communication between the first implantable medical device and the second implantable medical device.

The details of one or more aspects of the disclosure are set forth in the accompanying drawings and the description below. Other features, objects, and advantages of the disclosure will be apparent from the description and drawings, and from the claims.

DETAILED DESCRIPTION

Figure 1:
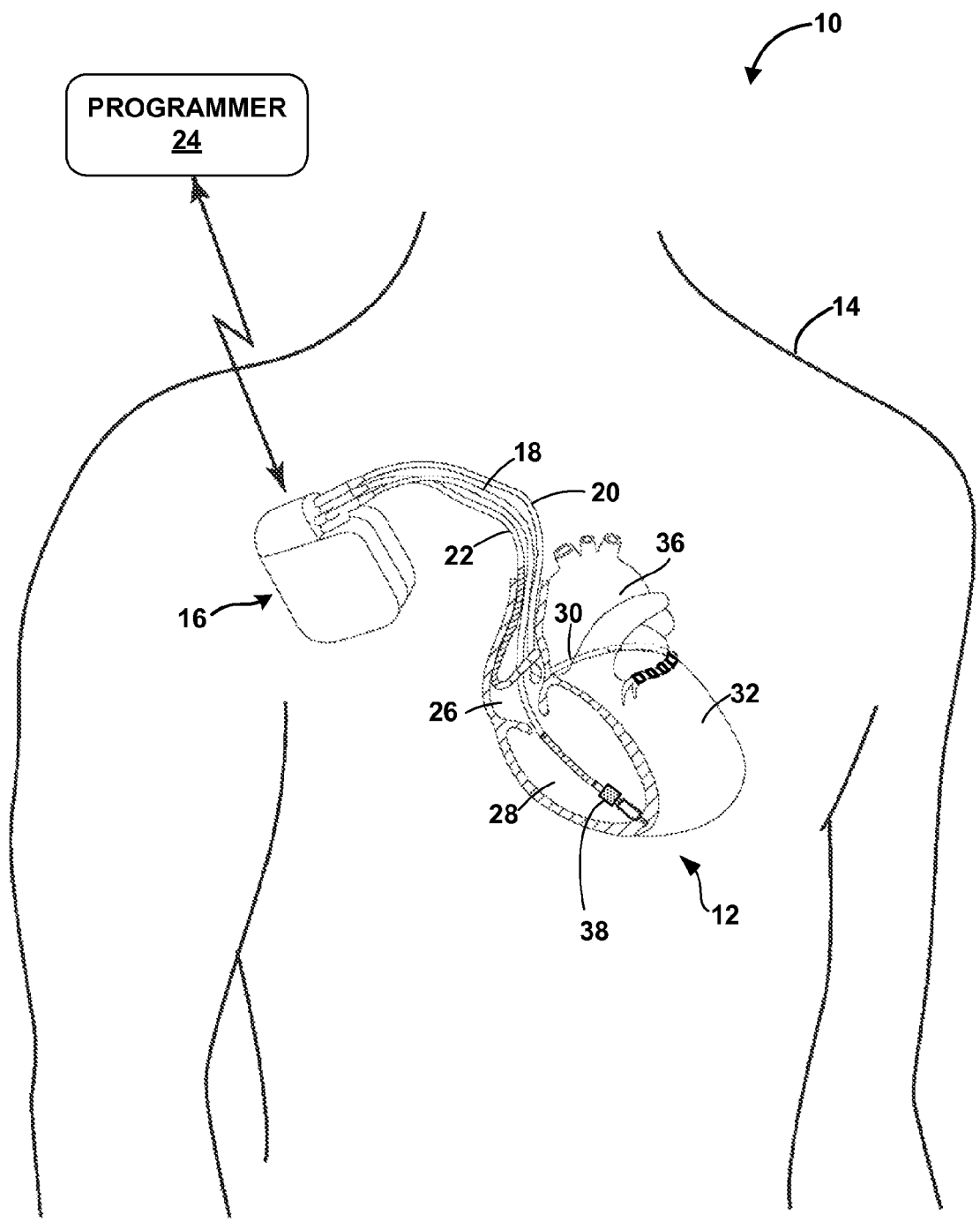
FIG. 1 is a conceptual diagram illustrating an example system that may be used to monitor one or more physiological parameters of a patient and/or to provide therapy to a heart of the patient.

Aspects of this disclosure are related to communication between a first implantable medical device (IMD) and a second IMD. The example implementations of this disclosure are described in the context of IMDs. However, aspects of this disclosure may be practiced by one or more external medical devices.

The first IMD may be coupled to one or more leads. The second IMD may be carried by one of the leads. As used in this disclosure, the second IMD being carried by one of the leads includes examples where the second IMD is within or on the lead. The second IMD may be considered as a lead-borne implantable medical device. As used in the disclosure, the second IMD may be referred to as a satellite, and the first IMD may be referred to as an IMD. Examples of the one or more satellites include, but are not limited to, a switching device, e.g., for electrodes, or sensor, such as an accelerometer, a strain gauge, a pressure sensitive-capacitor, an optical perfusion sensor, an oxygen saturation sensor, an ultrasonic flow sensor, a thermistor, or an antimony electrode.

In some examples, there may be more than one satellite on a lead. The satellites may be located at any position on the leads, e.g., including relatively distal or proximal positions.

The one or more leads may also include one or more electrodes for transmission of electrical stimulation signals and/or sensing of electrical signals within the patient. The IMD may be coupled to the electrodes via conductors within the leads that couple to the IMD and the electrodes. The IMD may include an impedance measurement module that measures the impedance of an electrical path that includes at least two of the electrodes. As a few examples, the impedance measurement module may measure the impedance of the electrical path that includes the at least two electrodes to monitor the functionality of the lead, e.g., monitor the electrical integrity of the lead, to monitor the impedance of tissue between the electrodes, or to determine whether there is fluid in a lung or lungs of a patient, e.g., to monitor edema. In some examples, the IMD may also include an electrode, such as an electrode on the housing of the IMD. The impedance measurement module may measure the impedance of a path that includes one of the electrodes formed on the lead and the electrode from on the IMD. The electrical path that includes at least two of the electrodes may include a conductor that extends from the IMD to a first electrode of the at least two electrodes, the first electrode, the tissue between the first electrode and a second electrode of the at least two electrodes, the second electrode, and a conductor that extends from the second electrode to the IMD.

In some of the example implementations described in this disclosure, the IMD may utilize the impedance measurement module to measure impedance and to communicate with the one or more satellites. For example, the IMD may program and/or interrogate the one or more satellites using the impedance measurement module.

For example, the impedance measurement module may include a current source or a voltage source, referred to as a source for illustration purposes, used for measuring impedance. The impedance measurement module may output an impedance measurement signal through at least two electrodes and measure the impedance of the electrical path including the at least two electrodes based on the impedance measurement signal. As one example, the source of the impedance measurement module may output a current through two electrodes, and measure the voltage between the two electrodes, or vice-versa. In this example, the outputted current or voltage may be the impedance measurement signal.

The impedance measurement module may also include a plurality of switches within a switch matrix, switch array, or a multiplexer (MUX), that may be configured to selectively couple the IMD to selected ones of the electrodes. The IMD may be able to transmit current or voltage to the electrodes, for impedance measurement, by closing appropriate switches. For example, a first electrode may be coupled to the impedance measurement module through a first switch and a second electrode may be coupled to the impedance measurement module through a second switch. The IMD may close the first and second switches. The IMD may then supply an impedance measurement signal that flows along the electrical path defined by the conductor associated with the first electrode, through the first electrode, through the patient's tissue, into the second electrode, and back to the IMD via the conductor associated with the second electrode for measurement of impedance of an electrical path including the first and second electrodes. In some examples, the first electrode may be an electrode on a lead coupled to the IMD, and the second electrode may be an electrode on the housing of the IMD, or vice versa. In some examples, the first electrode and the second electrode may be carried by the same lead. In some examples, the first electrode and the second electrode may be carried by different leads.

In some examples, in addition to impedance measurements, the IMD may utilize the source of the impedance measurement module to generate a communication signal for communication between the IMD and the one or more satellites. For instance, the IMD may utilize the source of the impedance measurement module to transmit signals to the one or more satellites. The one or more satellites may be coupled to the IMD via some of the same conductors that are used to couple the electrodes to the IMD. In other words, the one or more satellites may share a common conductor or signal bus with at least some of the electrodes.

As one example, to transmit information to the one or more satellites, the IMD may generate a bi-phasic communication signal. To generate the bi-phasic communication signal, the IMD may generate a bi-phasic pulse to represent a first binary value, e.g., a high or one. In the bi-phasic communication signal, an absence of a bi-phasic pulse may represent a second binary value, e.g., a low or zero. By generating the bi-phasic communication signal, the IMD may generate a stream of binary values with which the IMD may transmit information to the one or more satellites. In some examples, the frequency of the bit stream may be approximately 100 kilo-Hertz (kHz). However, aspects of this disclosure are not so limited. The frequency of the bit stream may be greater than or less than 100 kHz.

A single bi-phasic pulse may include two phases which may be a positive phase and negative phase. To generate the positive phase of a bi-phasic pulse, the IMD may modulate the amplitude of the current generated by the current source or the voltage generated by the voltage source to a positive voltage or current level. To generate the negative phase of the bi-phasic pulse, the IMD may modulate the amplitude of the current generated by the current source or the voltage generated by the voltage source to a negative voltage or current level.

To generate the negative voltage or current level, the IMD may swap the polarity of the voltage or current source. For example, to generate the positive current level, the IMD may source the current from the current source. To generate the negative current level, the IMD may sink the current from the current source.

As another example, to transmit information to the one or more satellites, the IMD may modulate the amplitude of the current generated by the current source or the voltage generated by the voltage source between a first amplitude level and a second amplitude level. In this example, the amplitude modulated current or voltage may be the generated communication signal. The first and second amplitude levels may be respectively associated with first and second binary values, e.g., a high or one and low or zero. By modulating the amplitude of the current or voltage, the IMD may generate a stream of binary values with which the IMD may transmit information to the one or more satellites. In some examples, the frequency of the bit stream may be approximately 100 kilo-Hertz (kHz). However, aspects of this disclosure are not so limited. The frequency of the bit stream may be greater than or less than 100 kHz.

As another example, to transmit information to the one or more satellites, the IMD may modulate the pulse width of the current pulses generated by the current source, or the voltage generated by the voltage source between a first pulse width and a second pulse width. In this example, the pulse width modulated current or voltage may be the generated communication signal. Similar to the amplitude levels, the first and second pulse widths may be respectively associated with first and second binary values. By modulating the pulse width, the IMD may generate a stream of pulses, that each represent either a high or low value, with which the IMD may transmit information to the one or more satellites.

As one example, to transmit information to the impedance measurement module of the IMD, the one or more satellites may similarly amplitude or pulse width modulate a current or voltage generate by a source within the satellites, or may similarly generate a bi-phasic communication signal. For example, the one or more satellites may include a communication generator that generates the amplitude or pulse width modulated signals, or the bi-phasic communication signal, for transmission to the impedance measurement module.

As another example, to transmit information to the impedance measurement module of the IMD, the one or more satellites may pull down a voltage placed on the conductor, by the impedance measurement module, that couples to the satellite at one of two pulse widths to indicate a logic high or one, or a logic low or zero. In this example, pulling down of the voltage may be considered as the generated communication signal because the source within the impedance measurement module may be utilized to generate the voltage that the satellite pull downs at two pulse widths to indicate the logical high or one, or the logic low or zero.

FIG. 1 is a conceptual diagram illustrating an example system 10 that may be used to monitor one or more physiological parameters of patient 14 and/or to provide therapy to heart 12 of patient 14. Therapy system 10 includes IMD 16, which is coupled to leads 18, 20, and 22, and wirelessly coupled to programmer 24. IMD 16 may be, for example, an implantable pacemaker, cardioverter, and/or defibrillator that provides electrical signals to heart 12 via electrodes coupled to one or more of leads 18, 20, and 22. IMD 16 may be considered as a first medical device. Patient 12 is ordinarily, but not necessarily, a human patient.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device, computer workstation, or networked computing device. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure or volume, which may be sensed via satellite 38, as one example. As another example, the user may use programmer 24 to retrieve information from IMD 16 regarding the performance or integrity of IMD 16 or other components of system 10, such as leads 18, 20 and 22, or a power source of IMD 16. As another example, the user may interact with programmer 24 to program, e.g., select parameters for, therapies provided by IMD 16, such as pacing, cardioversion and/or defibrillation.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

As illustrated in FIG. 1, lead 18 may include satellite 38. Satellite 38 may be a second implantable medical device. Satellite 38 may be a lead-borne implantable medical device that is carried by lead 18, e.g., on or within lead 18. Although only one satellite, e.g., satellite 38, is illustrated in FIG. 1, aspects of this disclosure are not so limited. In some instances, lead 18 may include more than one satellite 38. In some instances, one of leads 20 and 22 may include a satellite instead of lead 18. Also, in some instances, lead 18 may include satellite 38, and another lead or leads, e.g., lead 20 and/or 22, may include a satellite.

In some examples, satellite 38 may receive information from and transmit information to IMD 16. In some examples, satellite 38 may be a plurality of switches within a switch matrix, switch array, or a multiplexer (MUX). The plurality of switches may allow IMD 16 to couple to one or more electrodes on a lead. For example, IMD 16 may transmit a communication signal that causes the switches within satellite 38 to selectively couple to one or more of the electrodes on lead 18. In this manner, IMD 16 may transmit and receive signals from the one or more electrodes on lead 18.

Satellite 38 may reduce the number of conductors that need to traverse the full length of the lead 18. Satellite 38 may selectively, e.g., based on the impedance measurement module of IMD 16, couple a smaller number of proximal conductors to a greater number of distal conductors and associated electrodes or sensors of lead 18. In this manner, the portion of the lead proximal of satellite 38 may have fewer conductors, and thereby avoid or lessen the problems associated with increased numbers of conductors. As illustrated in FIG. 1, satellite 38 may be located relatively distally on lead 18, so that a larger, proximal portion benefits from fewer conductors. However, the example implementations of this disclosure should not be considered limited to requiring that satellite 38 be located at the distal end of lead 18.

In some examples, the various electrodes may be at different polarities. For example, IMD 16 may output a voltage between two electrodes, via satellite 38, causing one electrode to be at a positive polarity and another electrode to be at a negative polarity. As another example, via satellite 38, IMD 16 may measure voltage between two electrodes, designating one electrode as a positive electrode and another electrode as a negative electrode. Because satellite 38 may be configured to couple to electrodes that are at different polarities, satellite 38 may be considered as a multi-polar satellite.

In some examples, satellite 38 may be a sensor. For example, satellite 38 may be an accelerometer, a strain gauge, a pressure sensitive-capacitor, an optical perfusion sensor, an oxygen saturation sensor, an ultrasonic flow sensor, a thermistor, and an antimony electrode, as a few non-limiting examples. For instance, satellite 38 may measure pressure of heart 12, as one example. The pressure may be sensed at any suitable location within heart 12, such as within the right atrium 26, right ventricle 28, left atrium or left ventricle 32, or outside heart 12, such as within a blood vessel. As another example, satellite 38 may sense the amount of oxygen within the right atrium 26, right ventricle 28, left atrium or left ventricle 32, or outside heart 12, such as within a blood vessel. As yet another example, satellite 38 may determine whether patient 12 is moving, standing still, sitting or lying down, or standing up. Satellite 38 may also determine whether patient 12 is supine or prone when lying down.

The above functions of satellite 38 are provided for illustration purposes. Satellite 38 should not be considered limited to examples provided above. In general, satellite 38 may be any medical device, separate from IMD 16 that is in communication with IMD 16, e.g., transmits information to and/or receives information from IMD 16, via a conductor within lead 18. For example, satellite 38 may be a second implantable medical device that is a lead-borne medical device within or carried by one of leads 18, 20, and 22. Satellite 38 may be a sensor or a switch device that includes a plurality of switches for coupling IMD 16 to one or more electrodes, as two non-limiting examples.

In some examples, IMD 16 may communicate with satellite 38 utilizing the same circuitry that IMD 16 uses to measure impedance. For example, IMD 16 may include an impedance measurement module. The impedance measurement module may be configured to measure an impedance of an electrical path that includes two or more electrodes, which may be attached to one or more of leads 18, 20, and 22, and IMD 16. Furthermore, the impedance measurement module may be configured to transmit signals to and/or receive signals from satellite 38. In some example implementations of this disclosure, the circuitry that measures impedance may be the same circuitry that communicates with satellite 38.

In examples where satellite 38 is a switching device, IMD 16 may transmit a communication signal to satellite 38 that causes satellite 38 to selectively couple IMD 16 to various electrodes. In this example, the impedance measurement module of IMD 16 may transmit the communication signal to satellite 38 that causes satellite 38 to selectively couple the impedance measurement module of IMD 16 to one or more electrodes. As another example, in examples where satellite 38 is a sensor, IMD 16 may transmit a communication signal to or receive a communication signal from satellite 38 utilizing the impedance measurement circuit.

The example implementations of this disclosure may provide one or more advantages. For example, the impedance measurement module, already present within IMD 16 for the purpose of measuring impedance, may also be utilized for communication with satellite 38. In this manner, a manufacturer of implantable medical devices, such as IMD 16, may not need to include additional circuitry or interfaces for the IMD to communicate with satellites. The manufacturer of medical devices may be able to more easily modify the design of a preexisting medical device so that the medical device can communication with a satellite, such as satellite 38, even though the medical device was not originally configured to communicate with the satellite. Furthermore, the impedance measurement module may have been thoroughly tested for reliability. For example, the impedance measurement module may be thoroughly tested for measuring impedance to monitor the functionality of leads 18, 20, and 22 to ensure the electrical integrity of leads 18, 20, and 22, to monitor the impedance of tissue between the electrodes, or to determine whether there is fluid in a lung or lungs of patient 14, as a few non-limiting examples. By utilizing well tested circuitry, such as the impedance measurement module, the manufacturer may be confident that communication between IMD 16 and satellite 38 occurs with circuitry that is reliable.

Moreover, in some of the example implementations described in this disclosure, IMD 16 may communicate with satellite 38 without needing to be disconnected from any of the electrodes within the lead that carries satellite 38. For example, as illustrated in FIG. 1, satellite 38 may be carried by lead 18. In some of the examples, IMD 16 may communicate with satellite 38 while remaining coupled to the one or more electrodes carried by lead 18. In some of the examples, including satellite 38 within lead 18 may not require disconnecting any of the one or more electrodes carried by lead 18.

Figure 2:
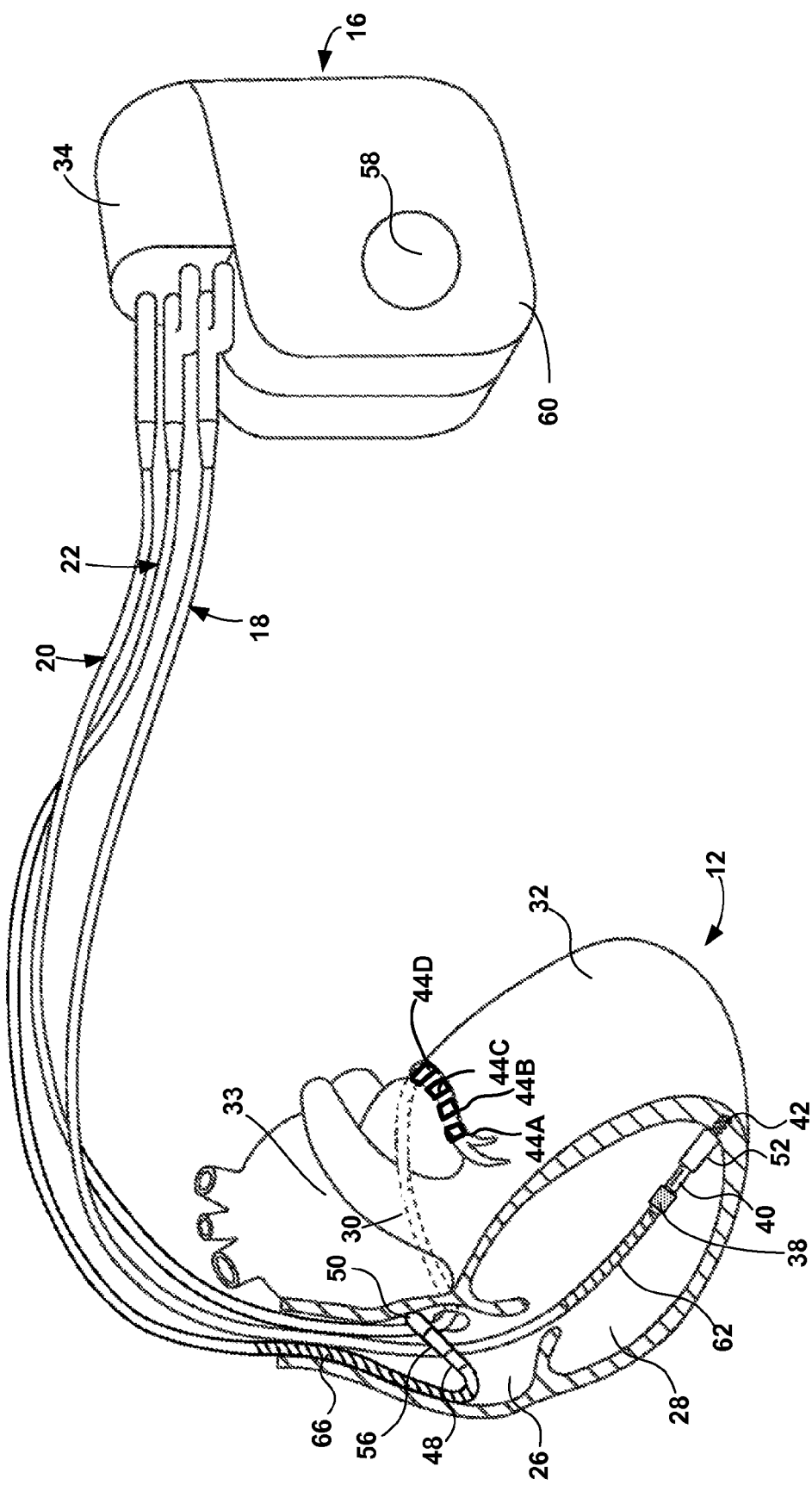
FIG. 2 is a conceptual diagram illustrating an implantable medical device (IMD) and leads of the system of FIG. 1 in greater detail.

FIG. 2 is a conceptual diagram illustrating IMD 16 and leads 18, 20, 22 of therapy system 10 in greater detail. Leads 18, 20, 22 may be electrically coupled to a signal generator, a sensing module, an impedance measurement module, or other modules of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. In the illustrated example, satellite 38 and bipolar electrodes 40 and 42 are located proximate to a distal end of lead 18 in right ventricle 28. In addition, bipolar electrodes 44 and 46 are located proximate to a distal end of lead 20 and bipolar electrodes 48 and 50 are located proximate to a distal end of lead 22.

In FIG. 2, satellite 38 is disposed in right ventricle 28. For purposes of illustration, satellite 38 may be configured to measure pressure. However, aspects of this disclosure should not be considered limited to examples where satellite 38 measures pressure. For example, satellite 38 may be configured as a switching device that allows IMD 16 to selectively couple to electrodes, e.g., electrodes 62, 40, and 42, on lead 18.

Satellite 38 may respond to an absolute pressure inside right ventricle 28, and may be, for example, a capacitive or piezoelectric absolute pressure sensor. In other examples, satellite 38 may be positioned within other regions of heart 12 and may monitor pressure within one or more of the other regions of heart 12, or may be positioned elsewhere within or proximate to the cardiovascular system of patient 14 to monitor cardiovascular pressure associated with mechanical contraction of the heart.

Electrodes 40, 44A-44D, and 48 may take the form of ring electrodes, and electrodes 42 and 50 may take the form of extendable helix tip electrodes mounted retractably within insulative electrode heads 52 and 56, respectively. Each of the electrodes 40, 42, 44A-44D, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44A-44D, 48 and 50 may sense electrical signals attendant to the depolarization and repolarization of heart 12. The electrical signals are conducted to IMD 16 via the respective leads 18, 20, 22. In some examples, IMD 16 also delivers pacing pulses via electrodes 40, 42, 44A-44D, 48 and 50 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44A-44D, 48 and 50 may be used for unipolar sensing or pacing in combination with housing electrode 58. As described in further detail with reference to FIG. 4, housing 60 may enclose a stimulation generator that generates cardiac pacing pulses and defibrillation or cardioversion shocks, as well as a sensing module for monitoring the patient's heart rhythm.

Leads 18 and 22 also include elongated electrodes 62 and 66, respectively, which may take the form of a coil. IMD 16 may deliver defibrillation pulses to heart 12 via any combination of elongated electrodes 62 and 66, and housing electrode 58. Electrodes 58, 62, and 66 may also be used to deliver cardioversion pulses to heart 12. Electrodes 62 and 66 may be fabricated from any suitable electrically conductive material, such as, but not limited to, platinum, platinum alloy or other materials known to be usable in implantable defibrillation electrodes.

Satellite 38 may be coupled to one or more conductors within lead 18. For example, satellite 38 may be coupled to one or more conductors within lead 18 that couple to one or more electrodes 40, 42, and 62. In FIG. 2, satellite 38 is located more distally on lead 18 than elongated electrode 62. In other examples, satellite 38 may be positioned more proximally than elongated electrode 62, rather than distal to electrode 62. Further, satellite 38 may be coupled to another one of the leads 20, 22 in other examples, or to a lead other than leads 18, 20, 22 carrying stimulation and sense electrodes.

Satellite 38 may be carried by lead 18 without requiring electrodes 40, 42, and 62 to be disconnected in lead 18. In other words, in some of the example techniques described in this disclosure, IMD 16 may communicate with satellite 38 while electrodes 40, 42, and 62 remain connected to IMD 16 via conductors within lead 18.

Any combination of electrodes 40, 42, 44A-44D, 48, 50, 60, 62, and 66 may be used for measuring impedance. In some examples a single pair of electrodes may be selected to generate an impedance measurement signal and to measure the impedance based on the impedance measurement signal. In some examples, the circuitry within IMD 16 that is configured to measure impedance between any combination of electrodes 40, 42, 44A-44D, 48, 50, 60, 62, and 66 may be the same circuitry that is used to communicate with satellite 38. For example, as described above, any combination of electrodes 40, 42, 44A-44D, 48, 50, 60, 62, and 66 may be used to generate an impedance measurement signal and to measure the impedance based on the impedance measurement signal. To generate the impedance measurement signal, IMD 16 may include a current source that generates current or a voltage source that generates voltage, referred to as a source for purposes of illustration. IMD 16 may transmit current, with the current source, through any combination of electrodes 40, 42, 44A-44D, 48, 50, 60, 62, and 66, or generate a voltage, with the voltage source, across any combination of electrodes 40, 42, 44A-44D, 48, 50, 60, 62, and 66 to generate the impedance measurement signal. The current source or the voltage source may be part of the impedance measurement module of IMD 16.

In some examples, IMD 16 may utilize the source of the impedance measurement module to generate a communication signal for communication between IMD 16 and satellite 38. To generate the communication signal for communication between IMD 16 and satellite 38, IMD 16 may generate a bi-phasic communication signal. The bi-phasic communication signal may include a bi-phasic pulse that may represent a first digital bit, e.g., a high or a one. In the bi-phasic communication signal, an absence of a bi-phasic pulse may represent a second digital bit, e.g., a low or a zero. By generating the bi-phasic communication signal, IMD 16 may utilize its impedance measurement module to generate a bit stream with which IMD 16 may transmit information to satellite 38.

One bi-phasic pulse may include a positive phase and a negative phase. The positive phase, of a bi-phasic pulse, may include a positive voltage or positive current. A positive current may be considered as instances where the source of the impedance measurement module is sourcing the current. The negative phase, of the bi-phasic pulse, may include a negative voltage or negative current. A negative voltage may indicate that the polarity of the source of the impedance measurement module is opposite to the polarity of the source of the impedance measurement module during the positive phase. A negative current may indicate that the source of the impedance measurement module is sinking the current.

As another example of generating the communication signal, IMD 16 may modulate an output of the source of the impedance measurement module. As one example, IMD 16 may modulate the amplitude of the current generated by the current source, or the voltage generated by the voltage source to generate first and second amplitude levels. The first and second amplitude levels may be indicative of respective first and second digital bits. By modulating the amplitude to generate first and second amplitude levels, IMD 16 may utilize its impedance measurement module to generate a bit stream with which IMD 16 may transmit information to satellite 38.

In some examples, the first amplitude level may be a positive amplitude level, e.g., greater than 0V or 0 A, and the second amplitude level may be a negative amplitude level, e.g., less than 0V or 0 A. In examples where IMD 16 modulates the voltage or current of the source to generate logic ones and zeros, IMD 16 may ensure that the number of ones is substantially equal to the number of zeros. In this manner, IMD 16 may not allow substantial amounts of charge to build up electrodes on the lead that carries satellite 38, e.g., electrodes 40, 42, and 62 on lead 18. However, it may not be necessary for IMD 16 to ensure that there are equal numbers of logic ones and logic zeros in all instances.

As another example of generating the communication signal, IMD 16 may generate a plurality of current pulses or voltage pulses from the current source or voltage source, respectively. IMD 16 may modulate the pulse widths of the pulses to generate first and second pulse widths. The first and second pulse widths may be indicative of respective first and second digital bits. By modulating the pulse widths to generate first and second pulse widths, IMD 16 may utilize its impedance measurement module to generate a bit stream with which IMD 16 may transmit information to satellite 38.

To receive information from satellite 38, IMD 16 may close at least the switch coupled to satellite 38. Satellite 38 may then be able to transmit information to IMD 16. In some examples, the switch that couples the data terminal of satellite 38 may be formed within the impedance measurement module of IMD 16. In this manner, IMD 16 may utilize its impedance measurement module to receive information from satellite 38. For example, satellite 38 may include pulse generation circuitry to generate communication pulses with selected amplitudes, durations, and polarities, as well as, bi-phasic communication signals. Satellite 38 may modulate the amplitude or duration of the pulses, for example, to represent logic highs or ones or logic lows or zeros, or generate bi-phasic communication signals in a manner substantially similar to the manner described above.

As another example, satellite 38 may not itself generate pulses for communication. In these instances, the impedance measurement module of IMD 16 may generate a voltage on the conductor that couples the data terminal of satellite 38 to IMD 16. Satellite 38 may pull down the voltage on the conductor that couples the data terminal of satellite 38 to IMD 16 at one of two pulse widths to indicate logic highs or ones or logic lows or zeros.

The configuration of system 10 illustrated in FIGS. 1 and 2 is merely one example. It should be understood that various other electrode and lead configurations for measuring impedance, transmitting information to, and receiving information from satellite 38 are within the scope of this disclosure. For example, a system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a system may include any suitable number of leads coupled to IMD 16, and each of the leads may extend to any location within or proximate to heart 12. Other examples of systems may include three transvenous leads located as illustrated in FIGS. 1 and 2, and an additional lead located within or proximate to left atrium 36. Additional examples of systems may include a single lead that extends from IMD 16 into right atrium 26 or right ventricle 28, or two leads that extend into a respective one of the right ventricle 26 and right atrium 26.

Furthermore, although FIGS. 1 and 2 illustrate satellite 38 being carried by a lead within heart 12, aspects of this disclosure are not so limited. In some examples, IMD 16 may be configured to deliver stimulation or sense signals from other locations within patient 14, e.g., other than heart 12. For example, IMD 16 may be configured to deliver stimulation to a spinal cord of patient 14, via leads coupled to IMD 16, to reduce pain perceived by patient 14. In these examples, one or more of the leads coupled to IMD 16 may include one or more satellites, such as satellite 38. In these examples, IMD 16 may communicate with the satellites utilizing the example techniques described in this disclosure. For instance, in examples where IMD 16 is not configured to stimulate heart 12 or sense signals from heart 12, IMD 16 may communicate with one or more satellites utilizing the impedance measurement module of IMD 16. An example of an IMD not coupled to the patient's heart is described in more detail with respect to FIG. 10.

Figure 3:
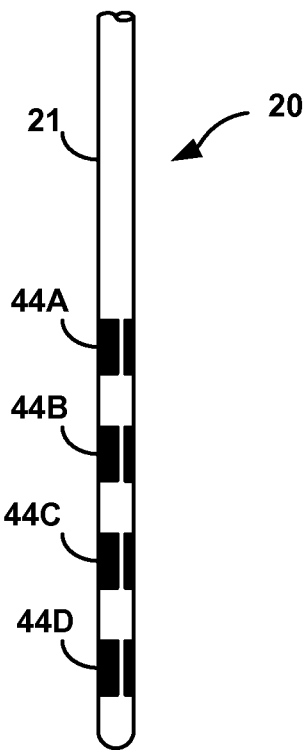
FIG. 3 is a conceptual diagram illustrating one example of an implantable lead.

FIG. 3 is a conceptual diagram illustrating one example of implantable lead 20. As illustrated in FIG. 3, lead 20 includes lead body 21. Lead 20 may be an example of a mulitpolar lead that includes four electrode levels, or bands mounted at various lengths of lead body 21. For example, electrodes 44A-44D may be electrodes that are mounted at four electrode levels, or bands at various lengths of lead body 21. Furthermore, each one of electrodes 44A-44D may include two or more electrodes. For example, electrodes 44A may include two or more electrodes, electrodes 44B may include two or more electrodes, and so forth. The electrodes of electrodes 44A-44D may be equally spaced along the axial length of lead body 21 at different axial positions. Each one of electrodes 44A-44D may include two or more electrodes located at different angular positions around the circumference of lead body 21.

Figure 4:
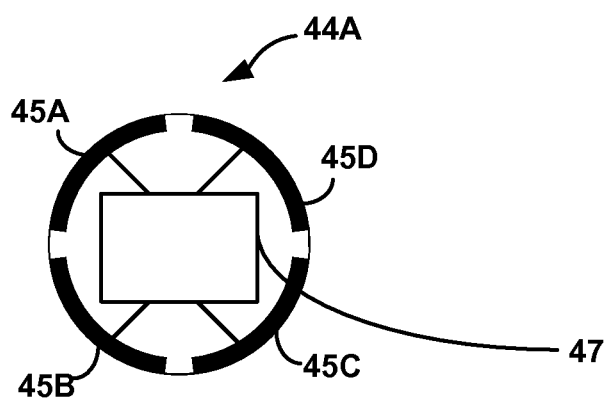
FIG. 4 is a transverse cross-section of an example lead having two or more electrodes around the circumference of the lead and a satellite coupled to the two or more electrodes.

FIG. 4 is a transverse cross-section of lead 20 having two or more electrodes around the circumference of lead 20 and satellite 47 coupled to the two or more electrodes. As illustrated in FIG. 4, electrodes 44A may include four electrodes 45A-45D. Electrodes 44B-44D may include similarly positioned electrodes. However, examples of this disclosure are not so limited. For instance, in some alternate implementations, electrodes 44A may include more or fewer electrodes than four electrodes. Moreover, electrodes 44A-44D need not all include the same number of electrodes. For example, electrodes 44A may include four electrodes, electrode 44B may include three electrodes, and electrodes 44C and 44D may each include two electrodes. There may be different permutations and combinations of the number of electrodes included in electrodes 44A-44D, and aspects of this disclosure should not be considered limited to the examples provided above.

As illustrated in FIG. 4, lead 20 may include satellite 47. Satellite 47 may be one example of a satellite. For example, satellite 47 may be a switching device that allows IMD 16 to selectively couple to one or more electrodes 45A-45D. Although FIG. 4 illustrates that lead 20 includes a single satellite 47, aspects of this disclosure are not so limited. In some examples, lead 20 may include more than one satellite 47. For instance, lead 20 may include satellite 47A-47D. In this example, satellite 47A may allow IMD 16 to selectively couple to one or more of electrodes 44A. Satellite 47B may allow IMD 16 to selectively couple to one or more of electrodes 44B, and so forth. Moreover, in some examples, lead 20 may include only a single satellite 47 that allows IMD 16 to selectively couple to one or more of electrodes 44A-44D. In general, any one of leads 18, 20, and 22 may include one or more of satellites, such as satellite 47, which allow IMD 16 to selectively couple to one or more electrodes carried by leads 18, 20, and 22.

In the example illustrated in FIG. 4, satellite 47 may allow IMD 16 to couple to electrodes 45A-45D. Because electrodes 45A-45D may be at different polarities, satellite 47 may be considered as a multi-polar satellite. As one example, satellite 47 may receive a communication signal from IMD 16. The communication signal may be a control signal that indicates to satellite 47 which ones of electrodes 45A-45D should be coupled to IMD 16. In response to the communication signal, satellite 47 may selectively couple the switches within satellite 47 to selectively couple electrodes 45A-45D as indicated by the communication signal. In some of the example implementations of this disclosure, the communication signal, transmitted by IMD 16, may be a communication signal transmitted by IMD 16 via the impedance measurement module of IMD 16.

Figure 5:
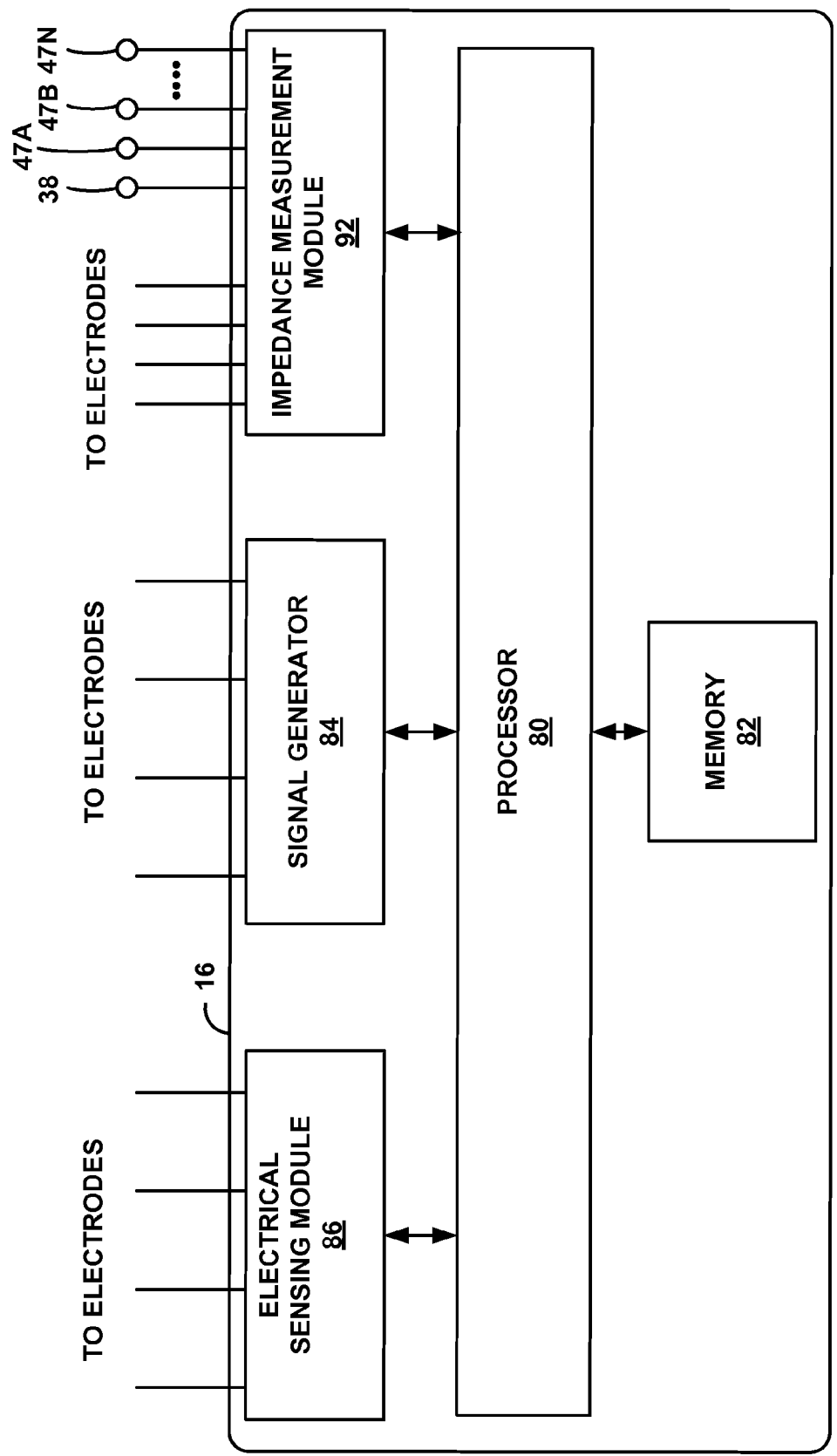
FIG. 5 is a functional block diagram illustrating one example configuration of an IMD.

FIG. 5 is a functional block diagram illustrating one example configuration of IMD 16. In the example illustrated by FIG. 4, IMD 16 includes a processor 80, memory 82, signal generator 84, sensing module 86, and impedance measurement module 92.

Memory 82 may include computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Memory 82 may, in some examples, be considered as a non-transitory storage medium. The term "non-transitory" may indicate that the storage medium is not embodied in a carrier wave or a propagated signal. However, the term "non-transitory" should not be interpreted to mean that memory 82 is non-movable or non-changeable. In certain examples, a non-transitory storage medium may store data that can, over time, change (e.g., in RAM).

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be formed as software or firmware executed on processor 80, hardware or any combination thereof.

In some example implementations of this disclosure, processor 80 may communicate with satellite 38 and/or one or more of satellites 47A-47N. To communicate with satellite 38 and/or one or more of satellites 47A-47N, processor 80 may generate a communication signal utilizing impedance measurement module 92. For example, processor 80 may amplitude or pulse width modulate a current or voltage generated by a source within impedance measurement module 92. As another example, processor 80 may generate a bi-phasic communication signal with the source within impedance measurement module 92.

As one example, processor 80 may generate the bi-phasic communication signal with the source within impedance measurement module 92. As described above, the bi-phasic communication signal may include a bi-phasic pulse that represents a logic high or one. An absence of a bi-phasic pulse, in the bi-phasic communication signal, may represent a logic low or zero. An example of a bi-phasic communication signal is described in more detail with respect to FIG. 7. By generating the bi-phasic communication signal, IMD 16 may utilize its impedance measurement module 92 to generate a bit stream with which IMD 16 may transmit information to satellite 38 and/or satellites 47A-47N.

As another example, processor 80 may modulate the amplitude of the current generated by the current source, or the voltage generated by the voltage source, of impedance measurement module 92, to generate first and second amplitude levels. The first and second amplitude levels may be indicative of respective first and second digital bits. In some examples, the number of first digital bits may be substantially the same as the number of second digital bits; however, aspects of this disclosure should not be considered so limiting. By modulating the amplitude to generate first and second amplitude levels, IMD 16 may utilize its impedance measurement module 92 to generate a bit stream with which IMD 16 may transmit information to satellite 38 and/or satellites 47A-47N.

As another example of generating the communication signal, processor 80 may generate a plurality of current pulses or voltage pulses from the current source or voltage source, respectively, of impedance measurement module 92. Processor 80 may modulate the pulse widths of the pulses to generate first and second pulse widths. The first and second pulse widths may be indicative of respective first and second digital bits. By modulating the pulse widths to generate first and second pulse widths, IMD 16 may utilize its impedance measurement module 92 to generate a bit stream with which IMD 16 may transmit information to satellite 38 and/or satellites 47A-47N.

To receive information from satellite 38 and/or satellites 47A-47N, impedance measurement module 92 may close at least the switch coupled to satellite 38 and/or satellites 47A-47N. Satellite 38 and/or satellites 47A-47N may then be able to transmit information to IMD 16. In some examples, the switch that couples to satellite 38 and/or satellites 47A-47N may be formed within impedance measurement module 92. In this manner, IMD 16 may utilize its impedance measurement module 92 to receive information from satellite 38 and/or satellites 47A-47N. For example, satellite 38 and/or satellites 47A-47N may include pulse generation circuitry to generate communication pulses with selected amplitudes, durations, and polarities, as well as, bi-phasic communication signals. Satellite 38 and/or satellites 47A-47N may modulate the amplitude or duration of the pulses, for example, to represent logic highs or ones or logic lows or zeros, or generate a bi-phasic communication signal to represent logic highs or ones or logic lows or zeros.

As another example, satellite 38 and/or satellites 47A-47N may not themselves generate pulses for communication. In these instances, impedance measurement module 92 may generate a voltage on the conductor that couples the data terminal of satellite 38 and/or satellites 47A-47N to IMD 16. Satellite 38 and/or satellites 47A-47N may pull down the voltage on the conductor that couples the data terminal of satellite 38 and/or satellites 47A-47N to IMD 16 at one of two pulse widths to indicate logic highs or ones or logic lows or zeros.

Processor 80 may communicate with satellite 38 and/or one or more of satellites 47A-47N for various purposes. As one example, processor 80 may cause impedance measurement module 92 to output a "wakeup" signal to satellite 38. In response to the wakeup signal, satellite 38 may perform its function. For example, as described above, satellite 38 may be an accelerometer, a strain gauge, a pressure sensitive-capacitor, an optical perfusion sensor, an oxygen saturation sensor, an ultrasonic flow sensor, a thermistor, and an antimony electrode. As a few examples, in response to the wakeup signal, satellite 38 may measure the pressure or oxygen, or determine the position of patient 12. Satellite 38 may then transmit the information back to processor 80, via impedance measurement module 92. Processor 80 may then utilize the received information to determine if any change to the therapy is desirable.

As another example, processor 80 may communicate with one or more of satellites 47A-47N, via impedance measurement module 92. For example, processor 80 may output one or more communication signals to one or more satellites 47A-47N instructing one or more satellites 47A-47N to selectively couple switches to one or more electrodes. In this manner, IMD 16 may couple to one or more electrodes that are coupled to one or more satellites 47A-47N.

Satellite 38 may be coupled to two conductors that are each associated with one electrode. For example, satellite 38 may be coupled to the conductors of electrodes 40 and 42. Satellites 47A-47N may be coupled to one or more electrodes. For example, satellite 47A may be coupled to electrodes 45A-45D of electrodes 44A. In some alternate examples, satellite 38 may be coupled to any one of electrodes 40, 42, 44A-44D, 48, 50, 58, 62, and 66 via the same conductor that couples one of electrodes 40, 42, 44A-44D, 48, 50, 58, 62, and 66 to IMD 16. Similarly, in some alternate examples, satellites 47A-47N may be coupled to one or more of electrodes 40, 42, 44A-44D, 48, 50, 58, 62, and 66 to allow IMD 16 to couple to one or more of electrodes 40, 42, 44A-44D, 48, 50, 58, 62, and 66.

Although FIG. 5 illustrates that impedance measurement module 92 is coupled to satellite 38 and satellites 47A-47N, aspects of this disclosure are not so limited. In some examples, leads 18, 20, and 22 may not include satellites 47A-47N, but may include satellite 38. In these examples, satellites 47A-47N may not be necessary. In some examples, none of leads 18, 20, and 22 may include satellite 38. In these examples, satellite 38 may not be necessary. Moreover, although satellites 47A-47N are illustrated in FIG. 5, in some examples, impedance measurement module 92 may be coupled to more or fewer satellites than satellites 47A-47N.

In addition to allowing processor 80 of IMD 16 to communicate with satellite 38 and/or satellites 47A-47N, impedance measurement module 92 may also be configured to measure impedance along the electrical path of any of the electrodes, e.g., electrodes 40, 42, 44A-44D, 48, 50, 58, 62, and 66. For example, impedance measurement module 92 may include circuitry to generate an impedance measurement signal along the electrical path between any two or more electrodes 40, 42, 44A-44D, 48, 50, 58, 62, and 66. Impedance measurement module 92 may be configured to measure the impedance based on the impedance measurement signal. In some of the example implementations, the circuitry used to generate the impedance measurement signal, in impedance measurement module 92, to measure impedance may be the same circuitry used to generate the communication signal, in impedance measurement module 92, to communicate with satellite 38 and/or satellites 47A-47N.

Although shown as separate modules in FIG. 5, in some examples, impedance measurement module 92 may be formed within signal generator 84 and sensing module 86. For example, one part of impedance measurement module 92 may be formed within signal generator, and the remaining part of impedance measurement module 92 may be formed within sensing module 86. For instance, impedance measurement module 92 may include a source for generating the impedance measurement signal and the communication signal. In this example, signal generator 84 may include the source of impedance measurement module 92. Impedance measurement module 92 may also include circuitry to measure the impedance along the electrical path between at least two electrodes and circuitry to receive communication signals from satellite 38 and/or satellites 47A-47N. In this example, sensing module 86 may include the circuitry to measure the impedance and to receive the communication signals.

In some alternate examples, impedance measurement module 92 may be fully formed within either signal generator 84 or sensing module 86. As one example, signal generator 84 may fully include impedance measurement module 92. As another example, sensing module 86 may fully include impedance measurement module 92. In yet some alternate examples, impedance measurement module 92 may be separate from signal generator 84 and sensing module 86, as illustrated in FIG. 5.

As illustrated in FIG. 5, electrical sensing module 86, signal generator 84, and impedance measurement module 92 are each coupled to conductors that are coupled to one or more electrodes. In some examples, electrical sensing module 86, signal generator 84, and impedance measurement module 92 may be coupled to the same conductors that are coupled to one or more electrodes. In these examples, electrical sensing module 86, signal generator 84, and impedance measurement module 92 may share the conductors, that couple to the electrodes, for their respective functions.

Processor 80 controls signal generator 84 to deliver stimulation therapy to heart 12 according to a selected one or more of therapy programs, which may be stored in memory 82. Signal generator 84 is electrically coupled to electrodes 40, 42, 44A-44D, 46, 48, 50, 58, 62, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple a signal to selected electrodes.

Electrical sensing module 86 monitors signals from at least one of electrodes 40, 42, 44A-44D, 48, 50, 58, 62, or 66 in order to monitor electrical activity of heart 12. Electrical sensing module 86 may also include a switch module to select which of the available electrodes are used to sense the heart activity. In some examples, processor 80 may select the electrodes that function as sense electrodes, or the sensing configuration, via the switch module within electrical sensing module 86, e.g., by providing signals via a data/address bus. Electrical sensing module 86 includes multiple detection channels, each of which may comprise an amplifier. In some examples, electrical sensing module 86 or processor 80 may include an analog-to-digital converter for digitizing the signal received from a sensing channel for processing by processor 80. In response to the signals from processor 80, the switch module within electrical sensing module 86 may couple the outputs from the selected electrodes to one of the detection channels.

Processor 80 may also control the timing of when impedance measurement module 92 communicates with satellite 38 and/or satellites 47A-47N. In some examples, when signal generator 84 outputs electrical stimulation via electrode 40 or 42, processor 80 may control impedance measurement module 92 to cease transmission of information to satellite 38 and cease reception of information from satellite 38. Because electrodes 40 and 42 and satellite 38 share a common conductor, electrical stimulation signals outputted via electrodes 40 and 42 may interfere with the transmission of information to or the reception of information from satellite 38. For example, as described above, stimulation generator 84 may deliver pacing pulses via electrodes 40 and 42. The pacing pulses may interfere with signals transmitted to or received from satellite 38 because satellite 38 and electrodes 40 and 42 share a common conductor.

Similarly, in examples where satellite 38 is coupled to one of the electrodes configured to deliver defibrillation shock, processor 80 may control impedance measurement module 92 not transmit information to satellite 38 when delivering the defibrillation shock. Processor 80 may also control impedance measurement module 92 to not receive information from satellite 38 when signal generator 84 is delivering the defibrillation shock. For example, assume that satellite 38 is coupled to electrode 62, rather than electrodes 40 and 42. As described above, signal generator 84 may deliver defibrillation shock via electrode 62. In this example, the defibrillation shock may interfere with signals transmitted to or received from satellite 38 because satellite 38 and electrode 62 share a common conductor.

In some examples, similar to satellite 38, processor 80 may cease communicating with satellites 47A-47N when signal generator 84 is utilizing the electrodes coupled to satellites 47A-47N for defibrillation shock or pacing pulses. For example, assume that satellite 47A is coupled to electrodes 45A-45D of electrodes 44A. Also, assume that processor 80 configures signal generator 84 to output a pacing pulse via electrodes 45A and 45B. In this example, processor 80 may first cause impedance measurement module 92 to transmit a communication signal to satellite 47A that causes satellite 47A to couple IMD 16 to electrodes 45A and 45B. Then, when signal generator 84 is transmitting the pacing pulse via electrodes 45A and 45B, processor 80 may cause impedance measurement module 92 to cease communicating with satellite 47A.

In some examples, impedance measurement module 92 may be configured to communicate with satellite 38 and/or satellites 47A-47N if signal generator 84 is outputting electrical stimulation via electrodes that are not coupled to satellite 38 and/or satellites 47A-47N. For example, if satellite 38 shares a common conductor with electrodes 40 and 42, if signal generator 84 is outputting electrical stimulation via any one or more of electrodes 44A-44D, 48, 50, 58, or 66, impedance measurement module 92 may communicate with satellite 38. Because electrodes 44A-44D, 48, 50, 58, or 66 do not share a common conductor with satellite 38, in this example, the electrical stimulation signals outputted via electrodes 44A-44D, 46, 48, 50, 58, or 66 may not interfere with the signals transmitted to or received from satellite 38.

In some of the example implementations of this disclosure, the signals generated to transmit information to or receive information from satellite 38 and/or satellites 47A-47N may not interfere with the functions of IMD 16. For instance, satellite 38 may share a common conductor with electrodes 40 and 42, or with some other electrode. It may be possible that because satellite 38 shares a common conductor with at least one of the electrodes, the generated communication signals for transmission of signals to or the reception of signals from satellite 38 may inadvertently affect heart 12. For example, as described above, processor 80 may amplitude modulate or pulse width modulate the current or voltage generated by impedance measurement module 92 to communicate with satellite 38, which shares a common conductor with electrodes 40 and 42. As described in more detail below, in some of the example implementations of this disclosure, the modulated amplitude or pulse width may not interfere with the pacing and defibrillating functions of IMD 16.

Pacing heart 12 may be referred to as capturing heart 12. To pace heart 12, signal generator 84 may need to generate a pulse with sufficient pulse width to capture heart 12. Processor 80 may select the pulse width of the modulated amplitude or pulse width signals to be less than the pulse width required to capture heart 12. For example, the pulse width of the modulated amplitude or modulated pulse width signals may be less than or equal to approximately 10 microseconds (us), as one non-limiting example. A pulse width of less than or equal to approximately 10 us may be insufficient to capture heart 12. In this manner, processor 80 may ensure that the signals of information transmitted to satellite 38 do not interfere with the pacing function of IMD 16.

To defibrillate heart 12, signal generator 84 may need to generate a pulse with sufficient amplitude to defibrillate heart 12. Processor 80 may select the amplitude of the modulated amplitude or pulse width signals to be less than the amplitude required to defibrillate heart 12. For example, the amplitude required to defibrillate heart 12 may be in order of tens or hundreds of volts. The amplitude of the modulated amplitude or pulse width signals may be in the order of milli-volts, as one non-limiting example. An amplitude in the order of milli-volts may be insufficient to defibrillate heart 12. In this manner, processor 80 may ensure that the signals of information transmitted to satellite 38 do not interfere with the defibrillation function of IMD 16.

The signals of information generated by satellite 38 and received by impedance measurement module 92 may also not interfere with the pacing and defibrillation functions of IMD 16. For example, the pulse width of the signals received from satellite 38 may be insufficient to capture heart 12. Also, the amplitude of the signals received from satellite 38 may be insufficient to defibrillate heart 12.

Figure 6A:
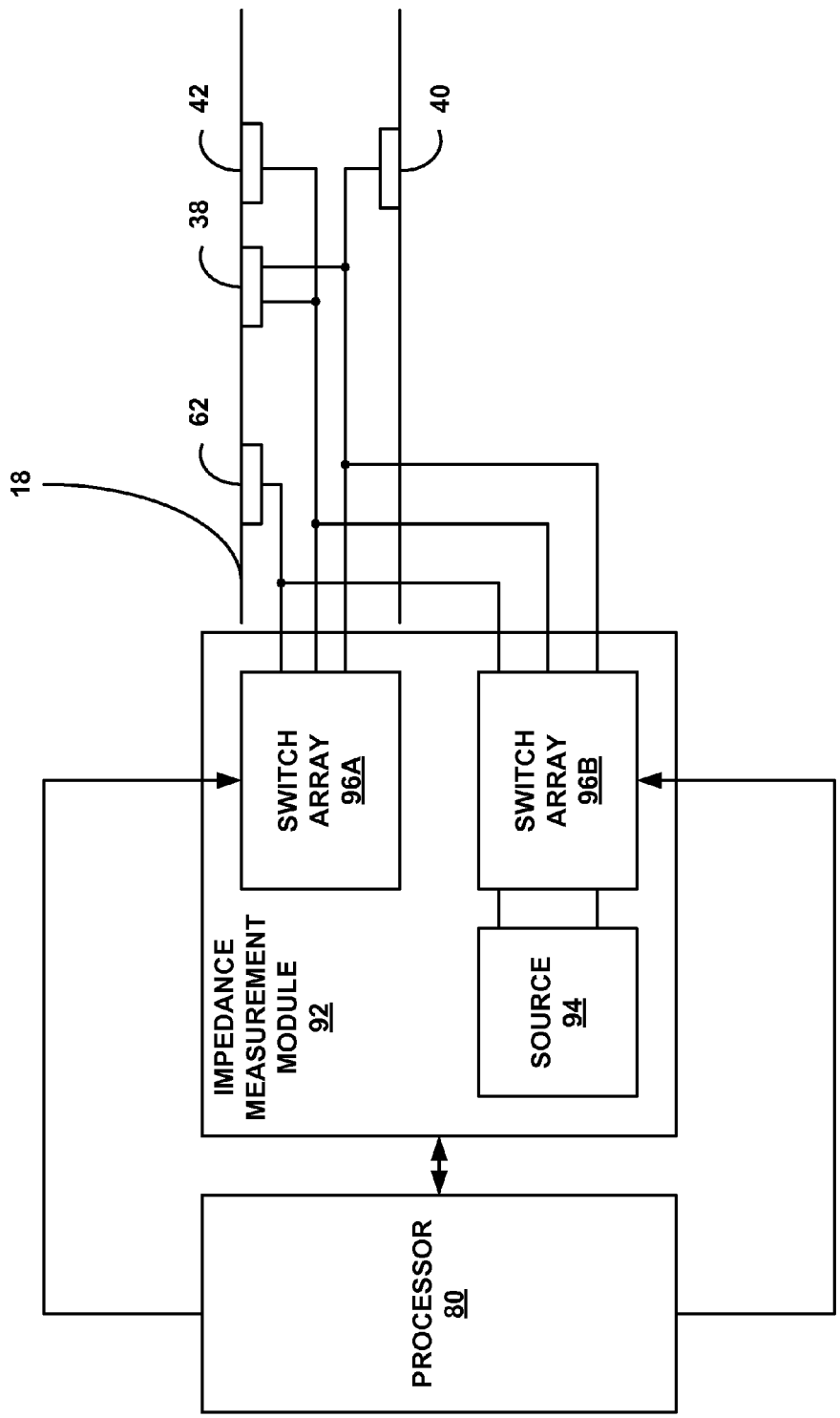
FIG. 6A is a functional block diagram illustrating an example of a satellite coupled to an impedance measurement module.

FIG. 6A is a functional block diagram illustrating an example of satellite 38 coupled to impedance measurement module 92. As illustrated in FIG. 6A, satellite 38 may be coupled to a distal end of lead 18. Lead 18 may include electrodes 40, 42, and 62, as illustrated in FIG. 2. Satellite 38 may be coupled to electrodes 40 and 42.

Electrodes 40, 42, and 62 and satellite 38 may be coupled to impedance measurement module 92 via switch array 96A and 96B. Although not shown in FIG. 6A, in some examples, part of impedance measurement module 92 may be formed within sensing module 86, and the remaining part of impedance measurement module 92 may be formed within signal generator 84. In some alternate examples, impedance measurement module 92 may be formed completely within sensing module 86 or signal generator 84. In some alternate examples, impedance measurement module 92 may be formed external to sensing module 86 and signal generator 84. Furthermore, although shown as separate components, in some examples, some or all of impedance measurement module 92 may be formed within processor 80.

Impedance measurement module 92 may be configured to measure impedance between any combinations of electrodes 40, 42, 44A-44D, 46, 48, 50, 58, 62, and 66. For purposes of illustration, impedance measurement module 92 is shown as being configured to measure impedance between any combination of electrodes 40, 42, and 62, in FIG. 6A Impedance measurement module 92 may include any one or more of a microprocessor, a controller, a DSP, an ASIC, a FPGA, or equivalent discrete or integrated logic circuitry. In some examples, impedance measurement module 92 may include multiple components, such as any combination of one or more microprocessors, one or more controllers, one or more DSPs, one or more ASICs, or one or more FPGAs, as well as other discrete or integrated logic circuitry. The functions attributed to impedance measurement module 92 herein may be formed as software or firmware executed on impedance measurement module 92, hardware or any combination thereof.

Impedance measurement module 92 may include source 94. Examples of source 94 include, but are not limited to, a current source or a voltage source. In examples where source 94 is a voltage source, source 94 may comprise a capacitor that is charged by a voltage source internal to processor 80, as one example. However, examples of this disclosure are not so limited. The voltage source internal to processor 80 may be approximately 1.4 volts, but again, examples of this disclosure are not so limited.

To measure impedance, source 94 may output an impedance measurement signal between any combinations of electrodes 40, 42, and 62 via switch array 96B. The impedance measurement signal may include current or voltage outputted by source 94. For example, source 94 may generate a current that flows through switch array 96B, out of electrode 40, through tissue of patient 12, back into electrode 42, through switch array 96B and back into source 94 to complete a full current path. In this example, impedance measurement module 92 may then measure a voltage along the path that includes electrodes 40 and 42 via switch array 96A. Impedance measurement module 92 may then divide the measured voltage with the current generated by source 94 to determine the impedance of the path that includes electrode 40 and 42, in this example.

Switch array 96A and 96B may each include at least one switch. Each switch, within switch array 96A and 96B, may allow impedance measurement module 92 to couple to electrodes 40, 42, and 62 and satellite 38. Switch array 96A and 96B may be controlled by processor 80. For example, to allow current to flow from electrode 40 to electrode 42, processor 80 may close switches within switch array 96B to couple source 94 to electrodes 40 and 42. To allow impedance measurement module 92 to measure the voltage between electrodes 40 and 42, processor 80 may close switches within switch array 96A to couple impedance measurement module to electrodes 40 and 42.

In some examples, as illustrated in FIG. 6A, switch array 96A and 96B may formed within impedance measurement module 92. In some examples, switch array 96A may be formed with sensing module 84, and switch array 96B may be formed within signal generator 86. In some examples, switch array 96A and 96B may be formed completely within sensing module 84 or within signal generator 86. Also, in some examples, switch array 96A and 96B may be formed outside of impedance measurement module 92. Furthermore, in some examples, switch array 96A and 96B may be formed within a common switch array, rather than separate switch arrays.

In addition to measuring impedance, impedance measurement module 92 may also allow processor 80 to communicate with satellite 38 via conductors coupled to satellite 38, switch array 96A, and switch array 96B. In some examples, impedance measurement module 92 may utilize the same components utilized for impedance measurements to communicate with satellite 38. For example, impedance measurement module 92 may utilize source 94 and switch array 96B to transmit information to satellite 38, and utilize switch array 96A to receive information from satellite 38.

Satellite 38 and processor 80 may be configured to communicate digitally with one another, as one example. For instance, satellite 38 may be configured to receive a bi-phasic communication signal where a bi-phasic pulse represents a logic one and an absence of a bi-phasic pulse represents a logic zero. As another example, satellite 38 may be configured to receive pulses at two different amplitudes, where one amplitude is indicative of a logic one and another amplitude is indicative of a logic zero. As another example, satellite 38 may be configured to receive pulses with two different pulse widths, where one pulse width is indicative of a logic one and another pulse width is indicative of a logic zero. Similarly, satellite 38 may be configured to transmit pulses at different amplitudes or pulse widths indicative of a logic one or a logic zero, as well as bi-phasic communication signals. Processor 80 may be configured to receive the pulses transmitted by satellite 38 via impedance measurement module 92. In this manner, satellite 38 and processor 80 may digitally communicate with one another.

In some examples, processor 80 may utilize source 94 of impedance measurement module 92 to generate a communication signal for communication between IMD 16 and satellite 38. To generate the communication signal for communication between IMD 16 and satellite 38, processor 80 may modulate an output of source 94 of impedance measurement module 92. As one example, processor 80 may modulate the amplitude of the current generated by source 94, in examples where source 94 is a current source, or the voltage generated by source 94, in examples where source 94 is a voltage source, between a positive amplitude level and a negative amplitude level to generate one bi-phasic pulse that represents a logic high.

The bi-phasic pulse may include a positive phase and a negative phase. In the example of FIG. 6A, impedance measurement module 92 may close switches within switch array 96B that are coupled to satellite 38 to generate the positive phase of a bi-phasic pulse. Impedance measurement module 92 may then open the switches within switch array 96B, and connect the switches within switch array 96B that couple to satellite 38 to generate the negative phase of the bi-phasic pulse. In this manner, impedance measurement module 92 may generate a single logic one. To generate multiple logic highs, impedance measurement module 92 may repeat the steps for generating the logic one, e.g., repeatedly generate a bi-phasic pulse. To generate a logic zero, impedance measurement module 92 may open the switches within switch array 96B and 96A that couple to satellite 38. In some examples the bit period for the logic one and logic zero may approximately 10 us. However, aspects of this disclosure are not so limited. In some examples the bit period may be less than 10 us or greater than 10 us. It may be desirable to select a bit period that is less than or equal to 10 us to ensure that communication signal does not inadvertently pace heart 12. In this manner, impedance measurement module 92 may generate a bi-phasic communication signal, which may be one example of a communication signal, to communicate with satellite 38.

As another one example, processor 80 may modulate the amplitude of the current generated by source 94, in examples where source 94 is a current source, or the voltage generated by source 94, in examples where source 94 is a voltage source, to generate first and second amplitude levels. The first and second amplitude levels may be indicative of respective first and second digital bits. By modulating the amplitude to generate first and second amplitude levels, processor 80 may utilize impedance measurement module 92 to generate a bit stream with which IMD 16 may transmit information to satellite 38.

For instance, to generate the amplitude modulated communication signal, processor 80 may close the switch within switch array 96B that is coupled to the conductors coupled to satellite 38, for a bit period, to generate a logic one. Processor 80 may open the switch within switch array 96B that is coupled to the conductors coupled to satellite 38, for the bit period, to generate a logic zero. In this manner, processor 80 may toggle the switch within switch array 96B to generate a bit stream that includes logic ones and zeros, with which source 94 of impedance measurement module 92 may generate a communication signal for communication between IMD 16 and satellite 38. In some examples the bit period for the logic one and logic zero may be approximately 10 us. However, aspects of this disclosure are not so limited. In some examples the bit period may be less than 10 us or greater than 10 us. It may be desirable to select a bit period that is less than or equal to 10 us to ensure that communication signal does not inadvertently pace heart 12.

As another example of generating the communication signal, processor 80 may modulate the output of source 94 to generate pulses with two different pulse widths, e.g., first and second pulse widths. The first and second pulse widths may be indicative of respective first and second digital bits. By modulating the pulse widths to generate first and second pulse widths, processor 80 may utilize source 94 of impedance measurement module 92 to generate a bit stream with which IMD 16 may communicate with satellite 38.

For instance, to generate the pulse width modulated communication signal, processor 80 may close the switch within switch array 96B that is coupled to the conductors coupled to satellite 38 for a first bit period, and then open the switch to generate a logic one. Processor 80 may close the switch within switch array 96B that is coupled to the conductors coupled to satellite 38 for a second bit period, and then open the switch to generate a logic zero. The first and second bit periods may be different, and may be less than or equal to approximately 10 us. The first and second bit periods may correspond to first and second pulse widths.

To receive information from satellite 38, processor 80 or satellite 38 may close at least the switch, within switch array 96A, that is coupled to the conductor that is coupled to satellite 38. Satellite 38 may then be able to transmit information to processor 80 through impedance measurement module 92. In some examples, the switch within switch array 96A that couples to satellite 38 may be formed within impedance measurement module 92, as illustrated in FIG. 6A. In this manner, processor 80 may utilize impedance measurement module 92 to receive information from satellite 38. For example, satellite 38 may include pulse generation circuitry to generate communication pulses with selected amplitudes, durations, and polarities. Satellite 38 may modulate the amplitude or duration of the pulses, for example, to represent logic highs or ones or logic lows or zeros, in some examples, and may be configured to generate bi-phasic communication signals in alternate examples.

As another example, satellite 38 may not itself generate pulses for communication. In these instances, source 94 of impedance measurement module 92 may generate a voltage on the conductors that couple to satellite 38. For example, processor 80 may close the switch with switch array 96B that couples to satellite 38 and the switch within switch array 96A that couples to satellite 38. Satellite 38 may pull down the voltage on the conductors that couple to satellite 38 to impedance measurement module 92 via switch array 96A at one of two pulse widths to indicate logic highs or ones or logic lows or zeros.

Digital communication between processor 80 and satellite 38 is described for illustration purposes and should not be considered as limiting. Processor 80 and satellite 38 may communicate with one another utilizing other communication techniques. Aspects of this disclosure may be extendable to any communication techniques between processor 80 and satellite 38 where impedance measurement module 92 is configured to measure impedance and to allow processor 80 and satellite 38 to communicate with one another.

Processor 80 may transmit various signals of information to satellite 38. As one example, processor 80 may transmit signals to program satellite 38. For instance, processor 80 may transmit signals to satellite 38 that cause satellite 38 to perform certain measurements at specified time intervals, and that cause satellite 38 to store the measurements. As another example, processor 80 may transmit signals to "wakeup" satellite 38. For instance, satellite 38 may be operating in low power mode, and may transition for low power mode to normal power mode in response to the "wakeup" signal. As yet another example, processor 80 may transmit a signal to satellite 38 that causes satellite 38 to perform a particular function. As still another example, processor 80 may transmit a signal to satellite 38 to request for the data stored in satellite 38, e.g., interrogate satellite 38.

Processor 80 may receive various signals of information from satellite 38. For example, in response to a wakeup signal, satellite 38 may transmit an acknowledgment signal to processor 80 indicating that satellite 38 is awake. As another example, in response to the interrogation by processor 80, satellite 38 may transmit some or all of the stored measurements. As yet another example, satellite 38 may transmit measurements to processor 80 during times defined by processor 80.

In some of the example implementations of this disclosure, processor 80 may utilize the measurements of satellite 38 to control the therapy provided to patient 14. For example, processor 80 may analyze the received measurements to identify progression of a disease or symptoms. In some cases, processor 80 may modify a delivered therapy based on the measurements. For example, in examples in which IMD 16 is a cardiac pacemaker, processor 80 may control or adjust one or more aspects of the pacing therapy delivered to patient 14, such as the aggressiveness of rate responsive pacing based on the measurements received from satellite 38. Furthermore, in some examples, processor 80 may cause IMD 16 to transmit the received measurements to programmer 24. Programmer 24 may then present the measurements to patient 14 or to the user of programmer 24.

In addition to receiving signals of information from and transmitting signals of information to satellite 38, processor 80 may also control the timing of when processor 80 and satellite 38 communicate with one another. For example, processor 80 may control the timing when processor 80 and satellite 38 communicate with one another based on the electrode or electrodes that share a common conductor with satellite 38. As illustrated in FIG. 6A, electrodes 40 and 42 and satellite 38 may share a common conductor.

In these instances, when processor 80 utilizes electrode 40 or 42 for transmission of stimulation signals, processor 80 may cease communication with satellite 38. When electrode 40 or 42 is outputting defibrillation or pacing signals, the defibrillation or pacing signals may interfere with the signals transmitted to satellite 38 because electrode 40 or 42 and satellite 38 share a common conductor. To avoid defibrillation or pacing signals from interfering with the signals transmitted to satellite 38, it may be desirable for processor 80 to cease communication with satellite 38 when electrode 40 or 42 is being used for stimulation purposes.

When electrodes, other than electrodes 40 or 42, are being used for stimulation purposes, e.g., electrode 62, processor 80 may communicate with satellite 38. For example, a defibrillation shock that is outputted by electrodes 62 may not interfere with the communication between satellite 38 and processor 80 because satellite 38 does not share a common conductor with electrode 62.

Moreover, communication between processor 80 and satellite 38 may not interfere with the functions of IMD 16. For example, it may be possible that when processor 80 transmits a signal to or receives a signal from satellite 38, that the signals may create an electric field around electrode 40 or 42 because electrode 40 and electrode 42 share a common conductor with satellite 38. The electric field may possibly capture or cause an arrhythmia of heart 12. To avoid the electric field from capturing or causing an arrhythmia of heart 12, processor 80 may transmit signals whose amplitudes and pulse widths are insufficient to capture heart 12. Also, the amplitude of the transmitted signal may be in the order of milli-volts, which may be insufficient to defibrillate heart 12. Similarly, satellite 38 may transmit signals of information whose amplitudes and pulse widths are insufficient to capture or cause an arrhythmia of heart 12.

Furthermore, as described above, in some examples, satellite 38 may be included within lead 18 without requiring IMD 16 to disconnect from electrodes 40, 42, and 62. In some examples, as described above, impedance measurement module 92 may be able to provide stimulation and sense signals with the conductors coupled to electrodes 40, 42, and 62, and use the same conductors for communication with satellite 38. In this manner, impedance measurement module 92 may communicate with satellite 38 without needing to disconnect from electrodes 40 and 42, even though electrodes 40 and 42 share a common conductor with satellite 38.

Figure 6B:
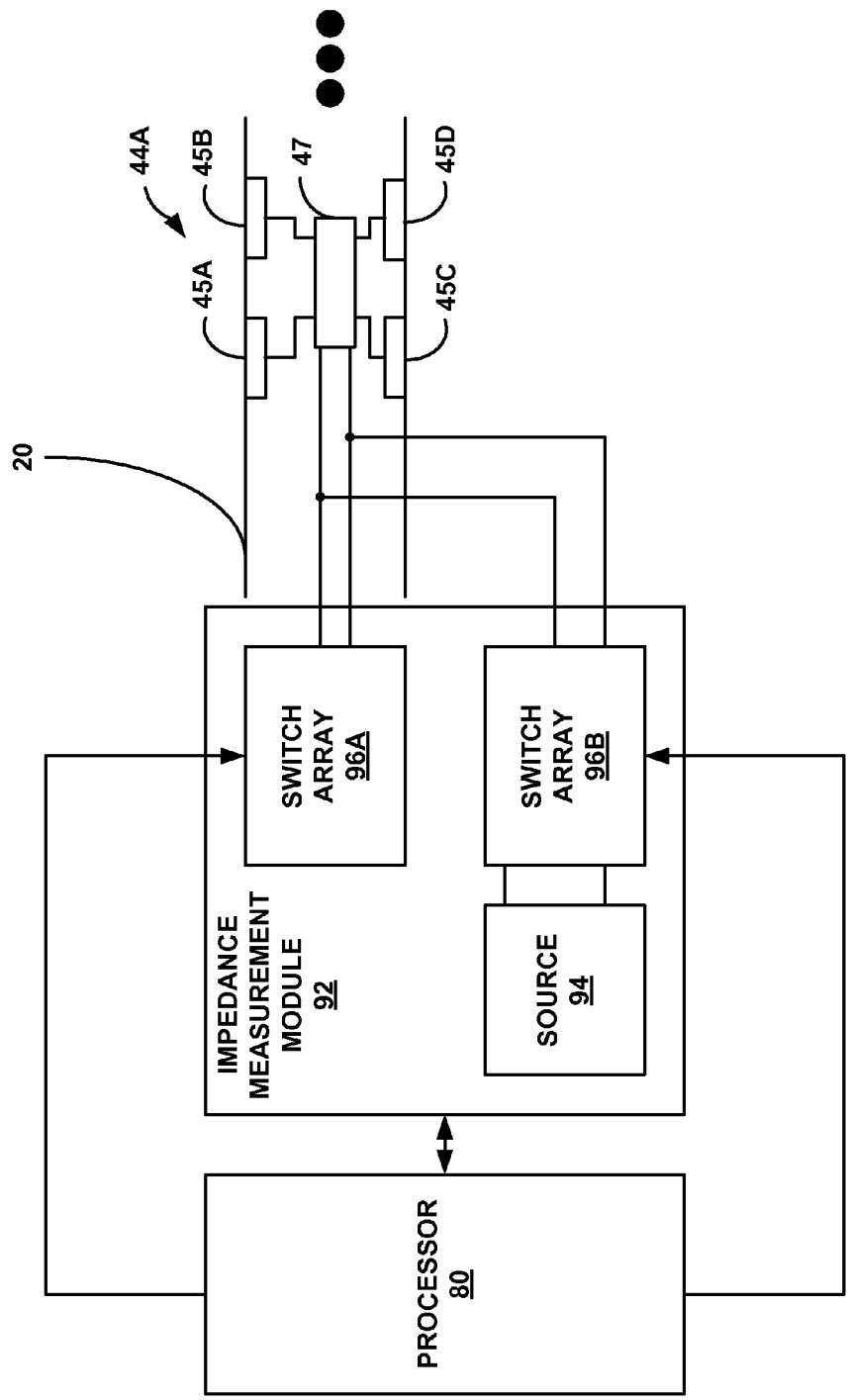
FIG. 6B is a functional block diagram illustrating another example of a satellite coupled to an impedance measurement module.

FIG. 6B is a functional diagram illustrating another example of satellite 47 coupled to impedance measurement module 92. In the example illustrated in FIG. 6B, impedance measurement module 92 is coupled to lead 20. Although FIG. 6B illustrates that impedance measurement module 92 is coupled lead 20, in some examples, impedance measurement module 92 may be coupled to lead 18, as illustrated in FIG. 6A, and 22.

As illustrated in FIG. 6B, switch array 96A and 96B may be coupled to conductors that couple to satellite 47. In this example, satellite 47 may be a switching device that allows IMD 16 to selectively couple to one or more of electrodes 45A-45D of electrodes 44A. Although a single satellite 47 is illustrated in FIG. 6B, in some examples, lead 20 may include more than one satellite, e.g., satellites 47B-47N.

In the example illustrated in FIG. 6B, processor 80 may generate a communication signal with impedance measurement module 92 in a manner substantially similar to the example described above with respect to FIG. 6A. In this example, processor 80 may generate the communication signal to instruct satellite 47 to selectively couple one or more of electrodes 45A-45D to IMD 16. As one example, processor 80 may be programmed to measure the impedance of the electrical path across electrodes 45A and 45D. In this example, processor 80 may transmit a communication signal, via source 84 and switch array 96B of impedance measurement module 92, instructing satellite 47 to couple electrodes 45A and 45D to IMD 16. After satellite 47 couples electrodes 45A and 45D to IMD 16, processor 80 may cause impedance measurement module 92, via source 94 and switch array 96B, to generate an impedance measurement signal. Processor 80 may then measure the impedance of the electrical path across electrodes 45A and 45D by closing the appropriate switches within switch array 96A. In this manner, processor 80 may communicate with satellite 47 utilizing the same circuitry that processor 80 utilizes to measure impedance, e.g., impedance measurement module 92.

Figure 7:
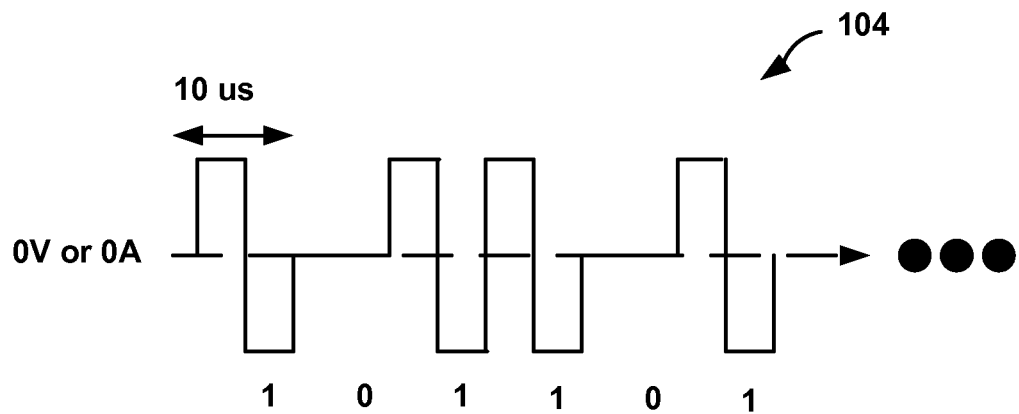
FIG. 7 is a timing diagram that illustrates communication between a processor and a satellite.

FIG. 7 is a timing diagram that illustrates communication between processor 80 and satellite 38 and/or satellite 47, e.g., satellites 47A-47N. For purposes of clarity, the example of FIG. 7 is described with satellite 38. However, the example of FIG. 7 should not be construed as limited to satellite 38.

As described above, to transmit signals of information to satellite 38, processor 80 may generate a bi-phasic communication signal. For example, processor 80 may open and close, e.g., toggle, appropriate switches within switch array 96B and 96A to generate the bi-phasic communication signal. Processor 80 may similarly receive signals from satellite 38. For example, satellite 38 may close appropriate switches within switch array 96A and 96B to transmit signals to processor 80 via impedance measurement module 92. As one example, FIG. 7 illustrates a timing diagram where processor 80 generates a b-phasic communication signal 104 utilizing source 94. As illustrated in FIG. 7, bi-phasic communication signal 104 may comprise digital bits 101101.

To generate the first logic one, e.g., a bi-phasic pulse, of bi-phasic communication signal 104, processor 80 may close a switch within switch array 96B that is coupled to satellite 38, to generate the positive phase of the logic one, and then close a switch within switch array 96A that is coupled to satellite 38 to generate the negative phase of the logic one, to generate one logic one bit. The positive phase, of a bi-phasic pulse, may be voltage or current that is greater than 0 volts or 0 amps. The negative phase, of a bi-phasic pulse, may be a voltage or current that is less than 0 volts or 0 amps. The absolute value of the voltage or current of the positive and negative phases may be substantially the same such that the average voltage or current of bi-phasic communication signal 104 is approximately 0 volts or 0 amps.

As illustrated in FIG. 7, the pulse width of the logic one may be approximately 10 us, as one example. A pulse width of approximately 10 us may be insufficient to capture heart 12. To generate a pulse width of approximately 10 us for the logic one, processor 80 may keep the switch within switch array 96B that is coupled to satellite 38 closed for approximately 10 us.

As illustrated in FIG. 7, processor 80 may then transmit a logic zero of digital signal 104. To transmit a logic zero, processor 80 may open the switch within switch array 96B that is coupled to satellite 38 and the switch within switch array 96A that is coupled to satellite 38 for approximately 10 us to generate a single logic zero, e.g., an absence of a bi-phasic pulse.

Processor 80 may then transmit two consecutive logic ones of bi-phasic communication signal 104. To transmit two consecutive logic ones, processor 80 may generate two consecutive bi-phasic pulses for a total of 20 us. Processor 80 may then transmit a logic zero and then a logic one of bi-phasic communication signal 104. To transmit a logic zero, processor 80 may open the switch within switch array 96B and 96A that is coupled to satellite 38 for approximately 10 us. Processor 80 may then generate another bi-phasic pulse to generate the logic one of bi-phasic communication signal 104.

The example illustrated in FIG. 7 is provided for illustration purposes only and should not be considered as limiting. For instance, bi-phasic communication signal 104 is not limited to 101101 as illustrated in FIG. 7. Moreover, processor 80 may transmit signals of information to satellite 38 utilizing pulse width modulation or amplitude modulation instead of a bi-phasic communication signal. Also, satellite 38 may transmit information to processor 80 in a substantially similar manner. For example, satellite 38 may include a current source or a voltage source that can be amplitude or pulse width modulated to communicate with processor 80. Also, satellite 38 may similarly generate a bi-phasic communication signal to communicate with processor 80. Furthermore, processor 80 and satellite 38 may generate signals of information utilizing other techniques than the examples provided in this disclosure.

Figure 8:
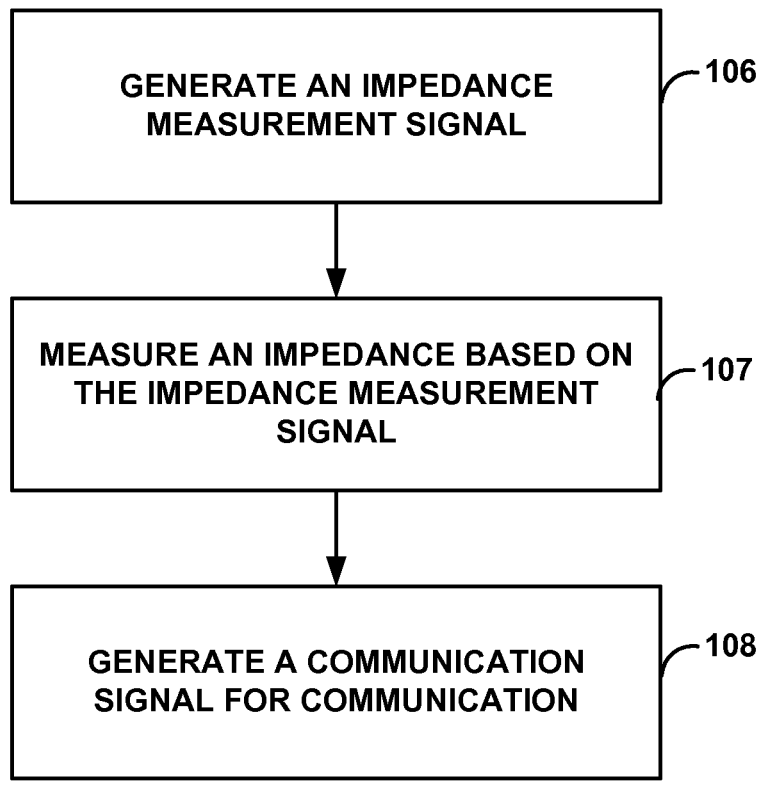
FIG. 8 is a flow diagram illustrating an example operation of an impedance measurement module within an IMD.

FIG. 8 is a flowchart illustrating an example operation of IMD 16. For purposes of illustration, reference is made to FIGS. 5, 6A, and 6B. In the example flowchart of FIG. 8, IMD 16 may be a first implantable medical device. For instance, a first medical device, e.g., IMD 16, may generate with source 94 of impedance measurement module 92, an impedance measurement signal (106). For example, the impedance measurement signal may be the current or voltage outputted by source 94 that is between any combination of electrodes 40, 42, 44A-44D, 48, 50, 58, 62, and 66.

IMD 16 may measure, with impedance measurement module 92, an impedance of an electrical bath that includes at least two electrodes, e.g., any two of electrodes 40, 42, 44A-44D, 48, 50, 58, 62, and 66 (107). In some examples, at least one of the two electrodes may be carried by a lead that is coupled to IMD 16, e.g., one of leads 18, 20, and 22.

Processor 80 of IMD 16 may generate, with source 94 of the impedance measurement module 92, a communication signal for communication between IMD 16 and a second implantable medical device that is within or carried by the lead that is coupled to IMD 16 (108). Examples of the second implantable medical device include satellite 38 and satellites 47A-47N. The second implantable medical device may be a lead-borne medical device that is carried by a lead, such as one of leads 18, 20, and 22, that is coupled to IMD 16. To communicate with satellite 38 or satellites 47A-47N, IMD 16 may utilize the same circuitry used to measure the impedance. For example, IMD 16 may utilize impedance measurement module 92 to communicate with satellite 38 or satellites 47A-47N. To communicate with satellite 38 or satellite 47A-47N, IMD 16 may transmit signals to or receive signals from satellite 38 or satellite 47A-47N.

For example, processor 80 may amplitude or pulse width modulate an output of source 94 to generate the communication signal. For instance, processor 80 may toggle the switch within switch array 96B that couples to satellite 38 to amplitude or pulse width modulate the output of source 94 to generate the communication signal. As another example, processor 80 may generate a bi-phasic communication signal with source 94 to generate the communication signal.

The example flowchart illustrated in FIG. 8 should not be construed to imply that IMD 16 must measure impedance before communicating with satellite 38 or satellites 47A-47N. In some examples, IMD 16 may communicate with satellite 38 or satellites 47A-47N before IMD 16 measures impedance. In some examples, IMD 16 may measure impedance, but may not communicate with satellite 38 or satellites 47A-47N. In some examples, IMD 16 may communicate with satellite 38 or satellites 47A-47N, and may not measure the impedance.

Figure 9:
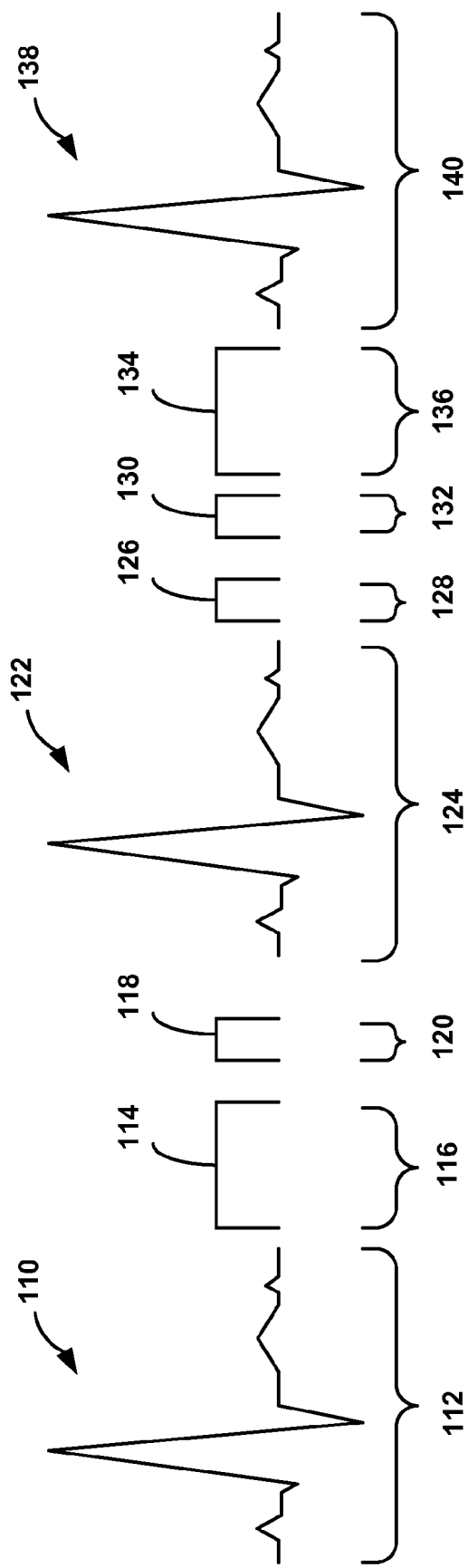
FIG. 9 is a timing diagram that illustrates instances of communication between an impedance measurement module and a satellite.

FIG. 9 is a timing diagram that illustrates instances of communication between impedance measurement module 92 and a satellite such as satellite 38 or one or more of satellites 47A-47N. FIG. 9 illustrates cardiac events 110, 122, and 138 at time periods 112, 124, and 140, respectively. One example of the cardiac event is a depolarization and repolarization event. FIG. 9 also illustrates communication events 114, 126, and 134 at time periods 116, 128, and 136, respectively. FIG. 9 also illustrates pacing events 118 and 130 at time periods 120 and 132 respectively. For purposes of illustration and clarity, it should be assumed that in the example of FIG. 9, the electrodes that are used to sense depolarization and repolarization and to transmit the pacing pulses are the same electrodes that are coupled to satellite 38 and/or satellites 47A-47N. Furthermore, it should be noted that although pacing pulses are illustrated, the example of FIG. 9 may be equally applicable to defibrillation shocks.

In some examples, processor 80 may be programmed to estimate the occurrences of the cardiac events such as depolarization and repolarization events 110, 122, and 138. As described above, sensing module 86 may be configured to sense the cardiac events.

In the example of FIG. 9, sensing module 86 may sense a depolarization and repolarization event 110 during time period 112. During time period 112, processor 80 may cease communication with satellite 38 and/or satellites 47A-47N. After depolarization and repolarization event 110, IMD 16 may transmit to or receive from satellite 38 and/or satellites 47A-47N communication event 114 during time period 116. IMD 16 may transmit to or receive from satellite 38 and/or satellites 47A-47N communication event 114 via impedance measurement module 92.

At time period 120, signal generator 84 may output pacing pulses during pacing event 118 to capture heart 12. During pacing event 118, processor 80 may cease communication with satellite 38 and/or satellites 47A-47N. After pacing event 118, sensing module 86 may sense the depolarization and repolarization event 122 during time period 124. During time period 124, processor 80 may cease communication with satellite 38 and/or satellites 47A-47N. After depolarization and repolarization event 124, IMD 16 may transmit to or receive from satellite 38 and/or satellites 47A-47N communication event 126 during time period 128. IMD 16 may transmit to or receive from satellite 38 and/or satellites 47A-47N communication event 126 via impedance measurement module 92.

At time period 128, signal generator 84 may output pacing pulses during pacing event 130 to capture heart 12. During pacing event 130, processor 80 may cease communication with satellite 38 and/or satellites 47A-47N. After pacing event 130, IMD 16 may transmit to or receive from satellite 38 and/or satellites 47A-47N communication event 134 during time period 136. IMD 16 may transmit to or receive from satellite 38 and/or satellites 47A-47N communication event 134 via impedance measurement module 92. After communication event 134, sensing module 86 may sense a depolarization and repolarization event 138 during time period 140.

Figure 10:
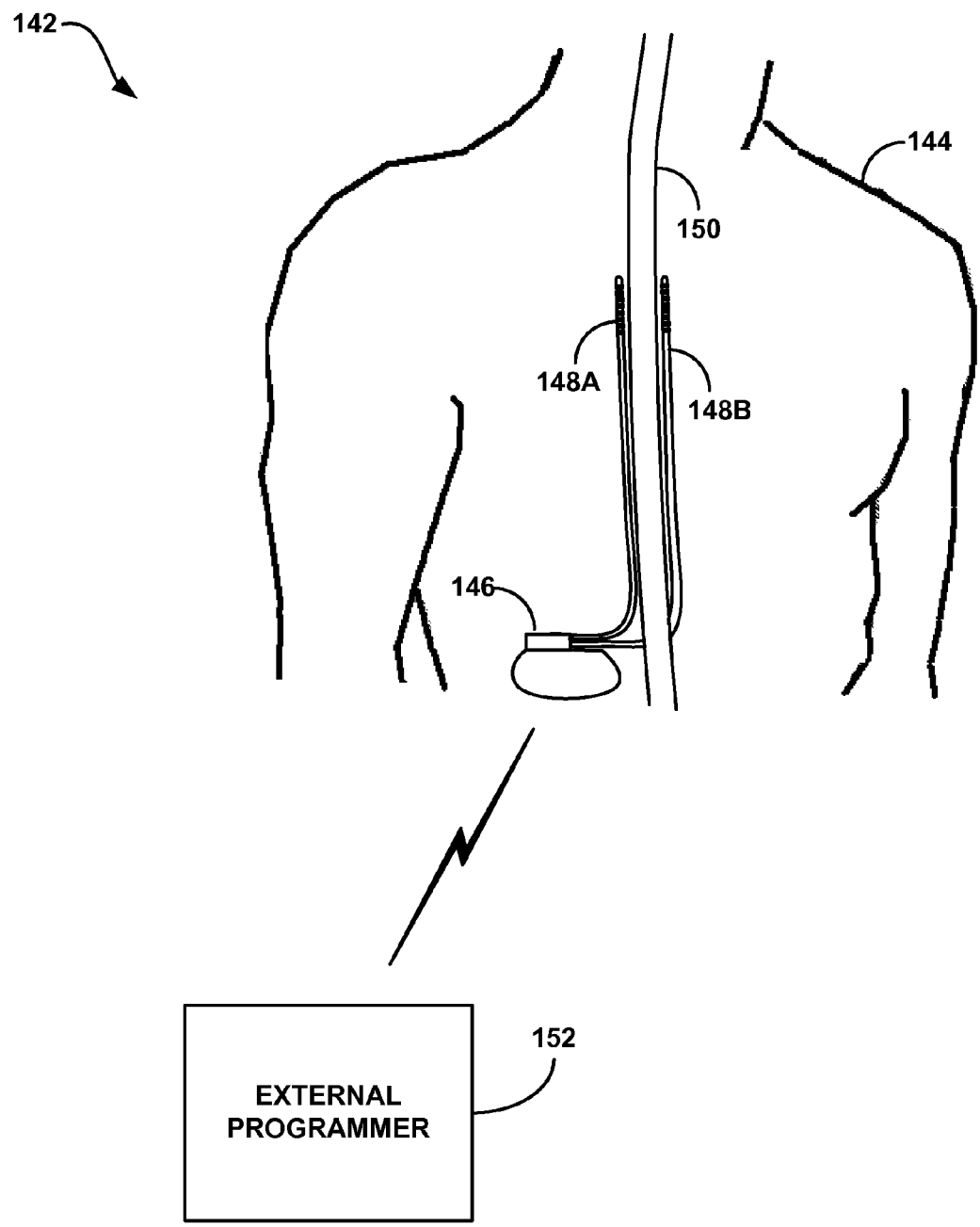
FIG. 10 is a conceptual diagram illustrating an example system that may be used to monitor one or more physiological parameters of a patient and/or to provide therapy to the patient.

FIG. 10 is a conception diagram illustrating an example system that may be use to monitor one or more physiological parameters of patient 144. As shown in FIG. 10, system 142 includes an implantable device 146 and an external programmer 152 shown in conjunction with patient 144. Implantable device 146 may be similar to IMD 16 (FIGS. 1 and 2). However, implantable device 146 may not deliver stimulation or sense signals from the heart of patient 144. In the example of FIG. 10, implantable device 146 may deliver stimulation to and sense signals from spinal cord 150 of patient 144. Although FIG. 10 shows an implantable device 146 coupled to fully implanted leads 148A, 148B, the techniques described in this disclosure may be applied to external stimulators coupled to leads via percutaneous lead extensions.

As shown in FIG. 10, leads 148A, 148B are implanted adjacent a spinal cord 150 of patient 144, e.g., for spinal cord stimulation (SCS) to alleviate pain. However, the techniques described in this disclosure are applicable to leads implanted to target any of a variety of target locations within patient 144, such as leads carrying electrodes located proximate to spinal cord 150, pelvic nerves, peripheral nerves, the stomach or other gastrointestinal organs, or within the brain of a patient.

In the example of FIG. 10, one or more of leads 148A, 148B may carry one or more satellites. For example, the satellites within one or more of leads 148A, 148B may be similar to satellite 38 or satellites 47A-47N (FIG. 5). In the example of FIG. 10, implantable device 146 may communicate with satellites carried by one or more leads 148A, 148B utilizing some of the example techniques of this disclosure. For example, implantable device 146 may utilize its impedance measurement module to measure impedance and communicate with one or more satellites carried by one or more leads 148A, 148B.

In the example of FIG. 10, stimulation energy is delivered from device 146 to spinal cord 150 of patient 144 via one or more electrodes carried by axial leads 148A and 148B (collectively "leads 148") implanted within patient 144. In various applications, such as spinal cord stimulation (SCS), the adjacent implantable leads 148 may have longitudinal axes that are substantially parallel to one another. Various combinations of electrodes carried by the leads 148 may be used to deliver electrical stimulation, including combinations of electrodes on a single lead or combinations of electrodes on both leads. Also, in some examples, electrodes may be carried by paddle leads in which an array of electrodes may be arranged in a two-dimensional pattern, e.g., as columns or rows of electrodes, on a common planar lead surface.

In the example of FIG. 10, leads 148 carry electrodes that are placed adjacent to the target tissue of spinal cord 150. In particular, leads 148 may be implanted in the epidural space adjacent spinal cord 150, and coupled to an implanted device 146. In the example of FIG. 10, stimulation energy may be delivered to spinal cord 150 to eliminate or reduce pain perceived by patient 144. However, device 146 may be used with a variety of different therapies, such as peripheral nerve stimulation (PNS), peripheral nerve field stimulation (PNFS), deep brain stimulation (DBS), cortical stimulation (CS), pelvic floor stimulation, gastric stimulation, and the like. The stimulation may be configured to alleviate a variety of symptoms or conditions such as chronic pain, tremor, Parkinson's disease, epilepsy, urinary or fecal incontinence, sexual dysfunction, obesity, or gastroparesis. The stimulation delivered by device 146 may take the form of stimulation pulses or continuous waveforms, and may be characterized by controlled voltage levels or controlled current levels, as well as pulse width and pulse rate in the case of stimulation pulses.

A user, such as a clinician, physician or patient 144, may interact with a user interface of external programmer 152 to program stimulator 146. Programming of device 152 may refer generally to the generation and transfer of commands, programs, or other information to control the operation of device 146. For example, programmer 152 may transmit programs, parameter adjustments, program selections, group selections, or other information to control the operation of device 146, e.g., by wireless telemetry. Parameter adjustments may refer to initial parameter settings or adjustments to such settings. A program may specify a set of parameters that define stimulation. A group may specify a set of programs that define different types of stimulation, which may be delivered simultaneously using pulses with independent amplitudes or on a time-interleaved basis.

Device 146 may be implanted in patient 144 at a location minimally noticeable to the patient. Alternatively, the device may be external to patient 144 and coupled to implanted leads via a percutaneous extension. For spinal cord stimulation (SCS), as an example, device 146 may be located, for example, in the lower abdomen, lower back, or other location to secure the stimulator. Leads 148 may be tunneled from device 146 through tissue to reach the target tissue adjacent to spinal cord 150 for stimulation delivery. At distal portions of leads 148 are one or more electrodes (not shown) that transfer stimulation energy from the lead to the tissue. The electrodes may be electrode pads on a paddle lead, circular (i.e., ring) electrodes, surrounding the body of leads 148, segmented electrodes arranged at different axial and rotational positions around a lead, conformable electrodes, cuff electrodes, or any other type of electrodes capable of forming unipolar, bipolar or multipolar electrode configurations.

Although the disclosure is described with respect to lead and electrode configurations implanted proximate to a heart, such techniques may be applicable to leads and electrodes implanted proximate to other areas within cardiovascular system such as, e.g., pulmonary arteries, pulmonary veins, the aorta, the vena cava, and the like. Moreover, the techniques described in this disclosure, including those attributed to image IMD 16, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following example statements.

The invention claimed is:

1. A method comprising:
generating, with a source of an impedance measurement module within a first implantable medical device, an impedance measurement signal;
measuring, with the impedance measurement module, an impedance of an electrical path that includes at least two electrodes based on the impedance measurement signal, wherein at least one of the electrodes is carried by a lead coupled to the first implantable medical device;
generating, with the source of the impedance measurement module, a threshold electrical signal transmitted from the first implantable medical device to a second implantable medical device that is carried by the lead; and
generating, by the second implantable medical device, a first communication signal that is derived from the threshold electrical signal for transmission to the first implantable medical device.

2. The method of claim 1, wherein generating the first communication signal comprises modulating the threshold electrical signal received from the first implantable medical device.

3. The method of claim 2, wherein modulating the threshold electrical signal comprises pulse width modulating.

4. The method of claim 3, wherein the pulse width modulating comprise a pull down of the threshold electrical signal at one of two pulse widths to generate the first communication signal as a binary signal.

5. The method of claim 1, further comprising generating a second communication signal, with the source of the impedance measurement module to transmit information to the second implantable medical device.

6. The method of claim 1, wherein the second implantable medical device is coupled to one of the at least two electrodes, the method further comprising:
transmitting an electrical stimulation signal via the one of the at least two electrodes; and
ceasing communication with the second implantable medical device during transmission of the electrical stimulation signal.

7. The method of claim 1 wherein the second implantable medical device is coupled to one of the at least two electrodes, the method further comprising:
estimating when a cardiac event will occur;
sensing the cardiac event with the one of the at least two electrodes; and
ceasing communication with the second implantable medical device during the sensing of the cardiac event.

8. The method of claim 1, wherein the second implantable medical device is at least one of an accelerometer, a strain gauge, a pressure sensitive-capacitor, an optical perfusion sensor, an oxygen saturation sensor, an ultrasonic flow sensor, a thermistor, and an antimony electrode.

9. The method of claim 1, wherein the second implantable medical device comprises a switching device.

10. The method of claim 5, wherein the second communication signal is communicated to the second implantable medical device without disconnecting the impedance measurement module from the at least two electrodes.

11. An implantable medical device comprising:
an impedance measurement module that comprises a source and is configured to generate an impedance measurement signal with the source, and measure an impedance of an electrical path that includes at least two electrodes based on the impedance measurement signal, wherein at least one of the electrodes is carried by a lead coupled to the implantable medical device;
a processor configured to generate, with the source of the impedance measurement module, a threshold electrical signal transmitted from the implantable medical device to a lead-borne implantable medical device that is carried by the lead; and
generating, by the lead-borne device, a first communication signal that is derived from the threshold electrical signal for transmission to the first implantable medical device.

12. The implantable medical device of claim 11, wherein the lead-borne device modulates the threshold electrical signal received from the first implantable medical device to generate the first communication signal.

13. The implantable medical device of claim 12, wherein modulating the threshold electrical signal comprises pulse width modulation.

14. The implantable medical device of claim 13, wherein the pulse width modulation comprises a pull down of the threshold electrical signal at one of two pulse widths to generate the first communication signal as a binary signal.

15. The implantable medical device of claim 11, wherein the processor is further configured to generate, with the source of the impedance measurement module, a second communication signal to transmit information to the lead-borne implantable medical device.

16. The implantable medical device of claim 11, wherein the lead-borne implantable medical device is coupled to one of the at least two electrodes, wherein the implantable medical device further comprises a signal generator configured to transmit an electrical stimulation signal via the one of the at least two electrodes, and wherein the processor is configured to cease communication with the lead-borne implantable medical device during transmission of the electrical stimulation signal.

17. The implantable medical device of claim 11, wherein the lead-borne implantable medical device is coupled to one of the at least two electrodes, wherein the processor is further configured to estimate when a cardiac event will occur, wherein the implantable medical device further comprises a sensing module configured to sense the cardiac event with the one of the at least two electrodes, and wherein the processor is configured to cease communication with the lead-borne implantable medical device during transmission of the electrical stimulation signal.

18. The implantable medical device of claim 11, wherein the implantable medical device is implanted within a patient.

19. The implantable medical device of claim 15, wherein the processor is configured to communicate the second communication signal without disconnecting the impedance measurement module from the at least two electrodes.

20. A medical system comprising:
a lead-borne implantable medical device that is carried by a lead;
an implantable medical device coupled to the lead-borne medical device via the lead, the implantable medical device comprising:
an impedance measurement module that comprises a source and is configured to generate an impedance measurement signal with the source, and measure an impedance of an electrical path that includes at least two electrodes based on the impedance measurement signal, wherein at least one of the electrodes is carried by a lead coupled to the implantable medical device; and
a processor configured to generate, with the source of the impedance measurement module, a threshold electrical signal transmitted from the implantable medical device to the lead-borne implantable medical device that is carried by the lead, wherein the lead-borne device generates a first communication signal derived from the threshold electrical signal for transmission to the first implantable medical device.

21. The medical system of claim 20, wherein generating the first communication signal comprises modulating the electrical signal received from the implantable medical device.

22. The medical system of claim 21, wherein the modulating the electrical signal comprises pulse width modulation.

23. The medical system of claim 22, wherein the pulse width modulation comprises a pull down of the electrical signal at one of two pulse widths to generate a binary communication signal.

24. The medical system of claim 20, the processor is further configured to generate, with the source of the impedance measurement module, a second communication signal to transmit information to the lead-borne implantable medical device.

25. The medical system of claim 20, wherein the lead-borne implantable medical device is coupled to one of the at least two electrodes, wherein the implantable medical device further comprises a signal generator configured to transmit an electrical stimulation signal via the one of the at least two electrodes, and wherein the processor is configured to cease communication with the lead-borne implantable medical device during transmission of the electrical stimulation signal.

26. The medical system of claim 20, wherein the lead-borne implantable medical device is coupled to one of the at least two electrodes, wherein the processor is further configured to estimate when a cardiac event will occur, wherein the implantable medical device further comprises a sensing module configured to sense the cardiac event with the one of the at least two electrodes, and wherein the processor is configured to cease communication with the lead-borne implantable medical device during transmission of the electrical stimulation signal.

27. The medical system of claim 20, wherein the lead-borne implantable medical device is at least one of an accelerometer, a strain gauge, a pressure sensitive-capacitor, an optical perfusion sensor, an oxygen saturation sensor, an ultrasonic flow sensor, a thermistor, and an antimony electrode.

28. The medical system of claim 20, wherein the lead-borne implantable medical device comprises a switching device.

29. The medical system of claim 20, wherein the implantable medical device is implanted within a patient, and the lead-borne implantable medical device is implanted within the patient.

30. The medical system of claim 24, wherein the processor is configured to generate the second communication signal for transmission to the lead-borne device without disconnecting the impedance measurement module from the at least two electrodes.

31. A computer-readable storage medium comprising instructions that cause one or more processors, within an implantable medical device, to:
  generate, with a source of an impedance measurement module within the implantable medical device, an impedance measurement signal;
  measure, with the impedance measurement module, an impedance of an electrical path that includes two electrodes based on the impedance measurement signal, wherein at least one of the electrodes is carried by a lead coupled to the implantable medical device;
  generate, with the source of the impedance measurement module, a threshold electrical signal transmitted from the implantable medical device to a lead-borne implantable medical device that is carried by the lead; and
  generating, by the lead-borne implantable medical device, a communication signal derived from the threshold electrical signal for transmission to the first implantable medical device.

* * * * *